United States Patent
Legrand

(10) Patent No.: US 7,578,854 B2
(45) Date of Patent: Aug. 25, 2009

(54) DYE COMPOSITION COMPRISING AT LEAST ONE FATTY ACID ESTER AND PROCESS FOR DYEING KERATIN FIBERS USING THE SAME

(75) Inventor: Frédéric Legrand, Tokyo (JP)

(73) Assignee: L'Oreal S.A., Paris (FR)

( * ) Notice: Subject to any disclaimer, the term of this patent is extended or adjusted under 35 U.S.C. 154(b) by 130 days.

(21) Appl. No.: 11/393,698

(22) Filed: Mar. 31, 2006

(65) Prior Publication Data

US 2006/0260069 A1 Nov. 23, 2006

Related U.S. Application Data

(60) Provisional application No. 60/681,172, filed on May 16, 2005.

(30) Foreign Application Priority Data

Mar. 31, 2005 (FR) .................... 05 50838

(51) Int. Cl.
*A61Q 5/10* (2006.01)
(52) U.S. Cl. .................. 8/405; 8/406; 8/407; 8/435; 8/552; 8/554; 8/580; 8/582
(58) Field of Classification Search .......... 8/405, 8/406, 407, 435, 552, 554, 580, 582
See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle | |
| 2,273,780 A | 2/1942 | Dittmar | |
| 2,375,853 A | 5/1945 | Kirby et al. | |
| 2,388,614 A | 11/1945 | Kirby et al. | |
| 2,454,547 A | 11/1948 | Bock et al. | |
| 2,961,347 A | 11/1960 | Floyd | |
| 3,206,462 A | 9/1965 | McCarty | |
| 3,227,615 A | 1/1966 | Korden | |
| 3,472,840 A | 10/1969 | Stone et al. | |
| 3,632,559 A | 1/1972 | Matter et al. | |
| 3,836,537 A | 9/1974 | Boerwinkle et al. | |
| 3,874,870 A | 4/1975 | Green et al. | |
| 3,910,862 A | 10/1975 | Barabas et al. | |
| 3,912,808 A | 10/1975 | Sokol | |
| 3,917,817 A | 11/1975 | Vanlerberghe et al. | |
| 3,929,990 A | 12/1975 | Green et al. | |
| 3,966,904 A | 6/1976 | Green et al. | |
| 3,986,825 A | 10/1976 | Sokol | |
| 4,001,432 A | 1/1977 | Green et al. | |
| 4,005,193 A | 1/1977 | Green et al. | |
| 4,013,787 A | 3/1977 | Varlerberghe et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,008 A | 5/1977 | Sokol | |
| 4,027,020 A | 5/1977 | Green et al. | |
| 4,031,307 A | 6/1977 | DeMartino et al. | |
| 4,075,136 A | 2/1978 | Schaper | |
| 4,131,576 A | 12/1978 | Iovine et al. | |
| 4,157,388 A | 6/1979 | Christiansen | |
| 4,165,367 A | 8/1979 | Chakrabarti | |
| 4,166,894 A | 9/1979 | Schaper | |
| 4,172,887 A | 10/1979 | Vanlerberghe et al. | |
| 4,189,468 A | 2/1980 | Vanlerberghe et al. | |
| 4,197,865 A | 4/1980 | Jacquet et al. | |
| 4,217,914 A | 8/1980 | Jacquet et al. | |
| 4,223,009 A | 9/1980 | Chakrabarti | |
| 4,240,450 A | 12/1980 | Grollier et al. | |
| 4,277,581 A | 7/1981 | Vanlerberghe et al. | |
| 4,348,202 A | 9/1982 | Grollier et al. | |
| 4,349,532 A | 9/1982 | Vanlerberghe et al. | |
| 4,381,919 A | 5/1983 | Jacquet et al. | |
| 4,422,853 A | 12/1983 | Jacquet et al. | |
| 4,445,521 A | 5/1984 | Grollier et al. | |
| 4,579,732 A | 4/1986 | Grollier et al. | |

(Continued)

FOREIGN PATENT DOCUMENTS

DE 30 30 119 11/1987

(Continued)

OTHER PUBLICATIONS

English language Derwent Abstract of DE 38 34 142 A1, Apr. 1990.
English language Derwent Abstract of EP 0 080 976 B1, Jun. 1983.
French search report for FR 05 50838 (Priority Application for U.S. Appl. No. 11/393,698), Nov. 4, 2005.
European search report for EP 06 11 1858 (European Counterpart to U.S. Appl. No. 11/393,698), Jul. 19, 2006.
Bruin, "Hydrophobically Modified Cellulos Ether for Personal Care." SOFW-Journal Seifen, Oeie, Fette, Wachse, Verlag fur Chemische Industri, Augsburg, DE, vol. 120, No. 15, Nov. 30, 1994, pp. 944-946, 948, XP000483287, ISSN: 0942-7694.
Copending U.S. Appl. No. 11/393,694, filed Mar. 31, 2006.
Copending U.S. Appl. No. 11/393,696, filed Mar. 31, 2006.
Copending U.S. Appl. No. 11/393,700, filed Mar. 31, 2006.
Copending U.S. Appl. No. 11/393,701, filed Mar. 31, 2006.
Copending U.S. Appl. No. 11/394,234, filed Mar. 31, 2006.

(Continued)

*Primary Examiner*—Eisa B Elhilo
(74) *Attorney, Agent, or Firm*—Finnegan, Henderson, Farabow, Garrett & Dunner, LLP

(57) ABSTRACT

The present disclosure relates to a dye composition comprising at least one dye, at least one nonionic surfactant, at least one cationic associative polymer, at least one fatty alcohol and at least one fatty acid ester, wherein the fatty alcohol/nonionic surfactant weight ratio is greater than 0.5 and water is present in the dye composition in an amount greater than or equal to 55% by weight. The disclosure also relates to a process for dyeing keratin fibers using such a composition, and also to a multi-compartment device or kit separately containing the dye composition and an oxidizing composition.

26 Claims, No Drawings

U.S. PATENT DOCUMENTS

| | | |
|---|---|---|
| 4,591,610 A | 5/1986 | Grollier |
| 4,608,250 A | 8/1986 | Jacquet et al. |
| 4,702,906 A | 10/1987 | Jacquet et al. |
| 4,719,099 A | 1/1988 | Grollier et al. |
| 4,719,282 A | 1/1988 | Nadolsky et al. |
| 4,761,273 A | 8/1988 | Grollier et al. |
| 4,777,040 A | 10/1988 | Grollier et al. |
| 4,803,221 A | 2/1989 | Bair |
| 4,839,166 A | 6/1989 | Grollier et al. |
| 4,919,923 A | 4/1990 | Hoeffkes et al. |
| 4,948,579 A | 8/1990 | Jacquet et al. |
| 4,970,066 A | 11/1990 | Grollier et al. |
| 4,996,059 A | 2/1991 | Grollier et al. |
| 5,009,880 A | 4/1991 | Grollier et al. |
| 5,057,311 A | 10/1991 | Kamegai et al. |
| 5,089,252 A | 2/1992 | Grollier et al. |
| 5,139,037 A | 8/1992 | Grollier et al. |
| 5,196,189 A | 3/1993 | Jacquet et al. |
| 5,480,459 A | 1/1996 | Mager et al. |
| 5,494,489 A | 2/1996 | Akram et al. |
| 5,708,151 A | 1/1998 | Mockli |
| 5,792,221 A | 8/1998 | Lagrange et al. |
| 5,958,392 A | 9/1999 | Grollier et al. |
| 5,990,233 A | 11/1999 | Barron et al. |
| 6,106,578 A | 8/2000 | Jones |
| 6,436,151 B2 * | 8/2002 | Cottard et al. ............... 8/406 |
| 6,540,791 B1 | 4/2003 | Dias |
| 6,613,315 B1 | 9/2003 | Dupuis |
| 6,800,098 B1 | 10/2004 | Allard et al. |
| 6,824,570 B2 | 11/2004 | Vidal et al. |
| 6,881,230 B2 | 4/2005 | Vidal |
| 6,884,265 B2 | 4/2005 | Vidal et al. |
| 6,884,267 B2 | 4/2005 | Vidal et al. |
| 6,893,471 B2 | 5/2005 | Vidal |
| 7,001,436 B2 | 2/2006 | Vidal et al. |
| 7,022,143 B2 | 4/2006 | Vidal et al. |
| 7,060,110 B2 | 6/2006 | Vidal et al. |
| 7,077,873 B2 | 7/2006 | David et al. |
| 7,261,743 B2 | 8/2007 | Plos et al. |
| 7,326,256 B2 | 2/2008 | Cottard et al. |
| 7,442,214 B2 | 10/2008 | Legrand |
| 2001/0023514 A1 | 9/2001 | Cottard et al. |
| 2002/0095732 A1 | 7/2002 | Kravtchenko et al. |
| 2003/0084516 A9 | 5/2003 | Kravtchenko et al. |
| 2003/0106169 A1 | 6/2003 | Vidal et al. |
| 2003/0124079 A1 | 7/2003 | Mougin et al. |
| 2003/0192134 A1 | 10/2003 | Desenne et al. |
| 2004/0047821 A1 | 3/2004 | Maubru et al. |
| 2004/0060126 A1 | 4/2004 | Cottard et al. |
| 2004/0093675 A1 | 5/2004 | Vidal et al. |
| 2004/0093676 A1 | 5/2004 | Vidal et al. |
| 2004/0098815 A1 | 5/2004 | Schmenger et al. |
| 2004/0107513 A1 | 6/2004 | Vidal et al. |
| 2004/0127692 A1 | 7/2004 | David et al. |
| 2004/0133995 A1 | 7/2004 | Cottard et al. |
| 2004/0141943 A1 | 7/2004 | Mougin et al. |
| 2004/0143911 A1 | 7/2004 | Vidal |
| 2004/0168263 A1 | 9/2004 | Vidal |
| 2004/0172771 A1 | 9/2004 | Cottard et al. |
| 2004/0180030 A1 | 9/2004 | Maubru |
| 2004/0187225 A1 | 9/2004 | Vidal et al. |
| 2004/0200009 A1 | 10/2004 | Vidal |
| 2004/0205902 A1 | 10/2004 | Cottard et al. |
| 2004/0216246 A1 | 11/2004 | Cotteret et al. |
| 2004/0244123 A1 | 12/2004 | Vidal et al. |
| 2005/0000039 A1 | 1/2005 | Audousset |
| 2005/0039268 A1 | 2/2005 | Plos et al. |
| 2005/0081311 A1 | 4/2005 | Schmenger et al. |

FOREIGN PATENT DOCUMENTS

| | | |
|---|---|---|
| DE | 38 34 142 A1 | 4/1990 |
| DE | 41 27 230 | 2/1993 |
| DE | 41 03 292 | 2/1994 |
| DE | 101 32 915 | 1/2003 |
| EP | 0 080 976 B1 | 6/1983 |
| EP | 0 122 324 B1 | 10/1984 |
| EP | 0 337 354 B1 | 10/1989 |
| EP | 0 412 706 | 2/1991 |
| EP | 0 714 954 B1 | 6/1996 |
| EP | 0 824 914 B1 | 2/1998 |
| EP | 0 825 200 A1 | 2/1998 |
| EP | 1 048 289 | 11/2000 |
| EP | 1 142 555 A1 | 10/2001 |
| EP | 1 174 450 A1 | 1/2002 |
| EP | 1 232 739 | 8/2002 |
| EP | 1 413 287 A1 | 4/2004 |
| EP | 1 426 032 | 6/2004 |
| EP | 1 426 039 A1 | 6/2004 |
| EP | 1 428 506 | 6/2004 |
| EP | 1 473 025 | 11/2004 |
| EP | 1 518 547 | 3/2005 |
| FR | 1 400 366 A | 5/1965 |
| FR | 1 492 597 A | 8/1967 |
| FR | 1 583 363 A | 10/1969 |
| FR | 2 077 143 A5 | 10/1971 |
| FR | 2 080 759 A1 | 11/1971 |
| FR | 2 162 025 A1 | 7/1973 |
| FR | 2 190 406 A2 | 2/1974 |
| FR | 2 252 840 A1 | 6/1975 |
| FR | 2 270 846 A1 | 12/1975 |
| FR | 2 280 361 A2 | 2/1976 |
| FR | 2 316 271 A1 | 1/1977 |
| FR | 2 320 330 A1 | 3/1977 |
| FR | 2 336 434 A1 | 7/1977 |
| FR | 2 368 508 A2 | 5/1978 |
| FR | 2 383 660 A1 | 10/1978 |
| FR | 2 393 573 A1 | 1/1979 |
| FR | 2 413 907 A1 | 8/1979 |
| FR | 2 470 596 A1 | 6/1981 |
| FR | 2 505 348 A1 | 11/1982 |
| FR | 2 519 863 A1 | 7/1983 |
| FR | 2 542 997 A1 | 9/1984 |
| FR | 2 598 611 A1 | 11/1987 |
| FR | 2 692 572 A1 | 12/1993 |
| FR | 2 717 076 | 9/1995 |
| FR | 2 795 312 | 12/2000 |
| FR | 2 803 195 | 7/2001 |
| FR | 2 807 650 A1 | 10/2001 |
| FR | 2 822 693 A1 | 10/2002 |
| FR | 2 822 694 A1 | 10/2002 |
| FR | 2 822 696 A1 | 10/2002 |
| FR | 2 822 698 A1 | 10/2002 |
| FR | 2 825 625 A1 | 12/2002 |
| FR | 2 825 702 A1 | 12/2002 |
| FR | 2 829 926 A1 | 3/2003 |
| FR | 2 833 833 | 6/2003 |
| FR | 2 844 269 A1 | 3/2004 |
| GB | 1021400 | 3/1966 |
| GB | 1 331 819 | 9/1973 |
| GB | 1 347 051 | 2/1974 |
| GB | 1 479 786 | 7/1977 |
| GB | 1546809 | 5/1979 |
| WO | WO 95/01772 | 1/1995 |
| WO | WO 95/15144 | 6/1995 |
| WO | WO 99/40893 | 8/1999 |
| WO | WO 00/68282 | 11/2000 |
| WO | WO 02/30370 | 4/2002 |
| WO | WO 02/45674 | 6/2002 |
| WO | WO 02/074271 A1 | 9/2002 |

| WO | WO 02/078660 A1 | 10/2002 |
| WO | WO 02/100369 A2 | 12/2002 |
| WO | WO 02/100834 A1 | 12/2002 |
| WO | WO 2004/019895 | 3/2004 |

OTHER PUBLICATIONS

English language Derwent Abstract for EP 1 048 289, dated Nov. 2, 2000.
English language Derwent Abstract of DE 101 32 915, dated Jan. 30, 2003.
English language Derwent Abstract of DE 30 30 119, dated Nov. 19, 1987.
English language Derwent Abstract of DE 41 03 292, dated Feb. 10, 1994.
English language Derwent Abstract of DE 41 27 230, dated Feb. 18, 1993.
English language Derwent Abstract of EP 1 232 739, dated Aug. 21, 2002.
English language Derwent Abstract of EP 1 518 547, dated Mar. 30, 2005.
English language Derwent Abstract of FR 2 795 312, dated Dec. 29, 2000.
European Search Report for EP 06 11 1856 (corresponding European counterpart application to U.S. Appl. No. 11/394,234), dated Jul. 19, 2006.
European Search Report for EP 06 11 1860 (corresponding European counterpart application to U.S. Appl. No. 11/393,701), dated Jul. 18, 2006.
European Search Report for EP 06 11 1861 (corresponding European counterpart application to U.S. Appl. No. 11/393,694), dated Jun. 14, 2006.
French Search Report for FR 05/50835 for U.S. Appl. No. 11/393,700, dated Nov. 3, 2005.
French Search Report for FR 05/50837 for U.S. Appl. No. 11/393,694, dated Nov. 10, 2005.
French Search Report for FR 05/50839 for U.S. Appl. No. 11/393,701, dated Nov. 9, 2005.
French Search Report for FR 05/50841 for U.S. Appl. No. 11/393,696, dated Feb. 14, 2006.
French Search Report for FR 05/50842 for U.S. Appl. No. 11/394,234, dated Feb. 15, 2006.
G. Fonnum, J. Bakke and Fk. Hansen—Colloid Polym. Sci. 271, 380-389 (1993).
Office Action mailed Jan. 7, 2008, in co-pending U.S. Appl. No. 11/393,694.
Office Action mailed Jan. 7, 2008, in co-pending U.S. Appl. No. 11/393,696.
Office Action mailed Jan. 7, 2008, in co-pending U.S. Appl. No. 11/393,700.
Office Action mailed Jan. 7, 2008, in co-pending U.S. Appl. No. 11/393,701.
Office Action mailed Jan. 7, 2008, in co-pending U.S. Appl. No. 11/394,234.
Office Action mailed Jun. 18, 2008, in co-pending U.S. Appl. No. 11/393,700.
Office Action mailed Jun. 23, 2008, in co-pending U.S. Appl. No. 11/393,694.
Office Action mailed Jun. 23, 2008, in co-pending U.S. Appl. No. 11/394,234.
Office Action mailed Jun. 27, 2008, in co-pending U.S. Appl. No. 11/393,701.
Office Action mailed Mar. 9, 2009, in co-pending U.S. Appl. No. 11/393,694.

* cited by examiner

DYE COMPOSITION COMPRISING AT LEAST ONE FATTY ACID ESTER AND PROCESS FOR DYEING KERATIN FIBERS USING THE SAME

This application claims benefit of U.S. Provisional Application No. 60/681,172, filed May 16, 2005, the contents of which are incorporated herein by reference. This application also claims benefit of priority under 35 U.S.C. § 119 to French Patent Application No. FR 05 50838, filed Mar. 31, 2005, the contents of which are also incorporated herein by reference.

The present disclosure relates to a dye composition comprising at least one dye, at least one nonionic surfactant, at least one cationic associative polymer, at least one fatty alcohol and at least one fatty acid ester; wherein the fatty alcohol/nonionic surfactant weight ratio is greater than 0.5 and water is present in the dye composition in an amount greater than or equal to 55% by weight relative to the weight of the dye composition. The present disclosure also relates to a process for dyeing keratin fibers using such a composition, and also to a multi-compartment device or kit comprising in at least one first compartment, a dye composition, and in at least one second compartment, an oxidizing composition.

There are essentially two types of dyeing of keratin fibers, including, for example, human keratin fibers such as the hair.

The first, known as oxidation dyeing or permanent dyeing, comprises using oxidation dye precursors, which are colorless or sparingly colored compounds. When they are placed in contact with an oxidizing agent, these compounds produce, via a process of oxidative condensation taking place within the fiber itself, colored substances that remain trapped in the fibers.

The second, known as direct dyeing or semi-permanent dyeing, is obtained by using colored and coloring compounds that have affinity for the keratin fibers onto which they are applied. This type of dyeing does not require the use of an oxidizing agent to reveal the color, although it is possible for this type of agent to be present during the process. The latter case is then referred to as lightening direct dyeing.

The known dye compositions are, in the majority of cases, in the form of liquids, gels or creams, which can be mixed, if necessary, before being applied to fibers, with an oxidizing composition.

Dye compositions are usually relatively rich in starting materials, among which are usually found fatty substances, surfactants and/or polymers. These compositions may be formulated such that they have spreading properties and textures that are easy to work with in order to allow quick and easy application to fibers, while at the same time being thick enough not to run beyond the areas that it is desired to color. Furthermore, these compositions should remain stable during the leave-on time on the fibers and should be easy to remove by rinsing once the coloration has been obtained.

It is not uncommon to find that large amounts of starting materials penalize the dyeing qualities of such compositions. Less favorable kinetics, a reduced intensity of the shade obtained, poorer homogeneity of the color from one fiber to another and/or depending on the location of the fiber (root/end), etc., may thus be observed.

There is thus a need for dye compositions that do not have the abovementioned drawbacks of the current dye compositions, while at the same time preserving the beneficial properties mentioned above.

Accordingly, the present disclosure relates to dye compositions that fulfill the need described above, comprising, in a medium that is suitable for dyeing keratin fibers:

at least one dye chosen from oxidation dye precursors and direct dyes;
at least one nonionic surfactant chosen from oxyalkylenated nonionic surfactants and glycerolated nonionic surfactants;
at least one cationic associative polymer;
at least one fatty alcohol;
at least one fatty acid ester of a $C_1$-$C_{10}$ alcohol;
wherein the fatty alcohol/nonionic surfactant weight ratio is greater than 0.5; and
further wherein water is present in the dye composition in an amount greater than or equal to 55% by weight, relative to the weight of the dye composition.

A further aspect of the present disclosure relates to a process for dyeing keratin fibers using such a composition, including, where appropriate, in the presence of an oxidizing composition.

The present disclosure also relates to a device comprising at least one first compartment containing a dye composition according to the present disclosure and at least one second compartment containing an oxidizing composition.

The composition according to the present disclosure may cause less degradation of the dyeing properties and allows stronger, more homogeneous and more chromatic colorations to be obtained, while at the same time giving the treated fibers good cosmetic properties and limiting their degradation.

The compositions in accordance with the present disclosure moreover may have an ideal texture for use in the dyeing of human keratin fibers, such as the hair. The compositions may be creamy, thick enough for quick and easy application, with good removal by rinsing, without, however, running beyond the areas of the hair that it is desired to treat.

Other characteristics and benefits of the present disclosure will emerge more clearly on reading the description and the examples that follow.

According to the disclosure, and unless otherwise indicated, it is pointed out that the limits of ranges of values are included in those ranges.

As used herein, the expression "at least one" is understood to mean one or more individual compounds, and also mixtures thereof.

When mention is made of a compound with a fatty chain, this chain may be a linear or branched, saturated or unsaturated hydrocarbon-based chain containing from 8 to 30 carbon atoms, such as, for example, from 10 to 24 carbon atoms.

Furthermore, the present disclosure is suitable for dyeing keratin fibers, including human keratin fibers, such as the hair.

Thus, the dye composition according to the present disclosure comprises water in an amount greater than or equal to 55% by weight, relative to the weight of the dye composition.

According to at least one embodiment of the present disclosure, water is present in an amount greater than or equal to 60% by weight, relative to the weight of the dye composition.

The composition according to the present disclosure may comprise at least one nonionic surfactant chosen from oxyalkylenated nonionic surfactants and glycerolated nonionic surfactants.

In at least one embodiment, the at least one nonionic surfactant chosen from oxyalkylenated nonionic surfactants and glycerolated nonionic surfactants can be chosen from:
oxyalkylenated or glycerolated fatty alcohols;
oxyalkylenated alkylphenols in which the alkyl chain is of $C_8$-$C_{18}$;
oxyalkylenated or glycerolated fatty amides;
oxyalkylenated plant oils;
optionally oxyalkylenated $C_6$-$C_{30}$ acid esters of sorbitan;
optionally oxyalkylenated fatty acid esters of sucrose;

fatty acid esters of polyethylene glycol;
$(C_6-C_{30})$alkylpolyglycosides;
N—$(C_6-C_{30})$alkylglucamine derivatives;
amine oxides, such as $(C_{10}-C_{14})$alkylamine oxides or N-acylaminopropylmorpholine oxides;
copolymers of ethylene oxide and of propylene oxide; and mixtures thereof.

In at least one embodiment, the mean number of oxyalkylene units may range from 2 to 150 units. The oxyalkylene units may be chosen from oxyethylene and oxypropylene units.

In at least one embodiment, the glycerolated surfactants may comprise on average from 1 to 20 glycerol groups, such as, for example, from 1.5 to 5 glycerol groups.

In accordance with at least one embodiment of the present disclosure, the composition may comprise at least one nonionic surfactant chosen from oxyalkylenated and/or glycerolated $C_6-C_{30}$ alcohols.

According to at least one embodiment of the present disclosure, the at least one nonionic surfactant may be present in an amount ranging from 0.01% to 50% by weight relative to the weight of the dye composition, such as, for example, from 0.5% to 40% by weight, relative to the weight of the dye composition.

According to at least one embodiment of the present disclosure, the composition also comprises at least one fatty alcohol. The at least one fatty alcohol may be non-oxyalkylenated and non-glycerolated.

In at least one embodiment, the at least one fatty alcohol is chosen from linear and branched, saturated and unsaturated $C_8-C_{30}$ alcohols, such as $C_{10}-C_{24}$ and $C_{12}-C_{24}$ alcohols, optionally comprising at least one other hydroxyl group.

Examples that may be mentioned, inter alia, include oleyl alcohol, lauryl alcohol, palmityl alcohol, myristyl alcohol, behenyl alcohol, stearyl alcohol, linoleyl alcohol, linolenyl alcohol, capryl alcohol and arachidonyl alcohol, or mixtures thereof.

According to at least one embodiment of the present disclosure, the at least one fatty alcohol may be present in an amount ranging from 0.1% to 30% by weight of the dye composition. For example, the at least one fatty alcohol may be present in an amount ranging from 0.5% to 20% by weight, relative to the weight of the dye composition.

In at least one embodiment of the present disclosure, the fatty alcohol/nonionic surfactant weight ratio may be greater than 0.5, such as, for example greater than 0.75.

The composition according to the present disclosure further comprises at least one fatty acid ester of a $C_1-C_{10}$ alcohol.

In at least one embodiment, the at least one fatty acid ester of a $C_1-C_{10}$ alcohol is chosen from monoesters, diesters and triesters of linear and branched, saturated and unsaturated $C_8-C_{30}$ carboxylic acids and of linear and branched, saturated and unsaturated $C_1-C_{10}$ monohydroxylated and polyhydroxylated alcohols.

In at least one embodiment, the at least one fatty acid ester of a $C_1-C_{10}$ alcohol is chosen from the monoesters, diesters and triesters of oleic acid, lauric acid, palmitic acid, myristic acid, behenic acid, stearic acid, linoleic acid, linolenic acid, capric acid, and arachidonic acid, and of methanol, ethanol, propanol, isopropanol, ethylene glycol, glycerol, octanol and decanol, and also mixtures thereof.

According to at least one embodiment of the present disclosure, the at least one fatty acid ester of a $C_1-C_{10}$ alcohol may be present in an amount ranging from 0.1% to 20% by weight relative to the weight of the dye composition. For example, the at least one fatty acid ester of a $C_1-C_{10}$ alcohol may be present in an amount ranging from 0.5% to 15% by weight relative to the weight of the dye composition.

The composition according to the present disclosure also comprises at least one cationic associative polymer.

The chemical structure of the at least one cationic associative polymer comprises hydrophilic regions that provide solubility in water, and hydrophobic regions via which the polymers, in an aqueous medium, assemble with each other or with the hydrophobic parts of other molecules. Such polymers are also capable, in an aqueous medium, of reversibly associating with each other or with other molecules.

In at least one embodiment, the at least one cationic associative polymer used in the compositions of the present disclosure may comprise amphiphilic polymers comprising at least one fatty chain.

For the purposes of the present disclosure, the term "polymer" is understood to mean compounds having in their structure a repetition of at least one sequence other than the ethylene oxide or propylene oxide or glycerol sequence if this type of sequence is present.

In at least one embodiment, the at least one cationic associative polymer present in the composition is chosen from quaternized cellulose derivatives, cationic polyurethanes, cationic polyvinyllactams and cationic acrylic terpolymers; these compounds comprising at least one fatty chain.

Quaternized Cellulose Derivatives

In at least one embodiment, these polymers may be chosen from:
quaternized celluloses modified with groups comprising at least one fatty chain, such as alkyl, arylalkyl or alkylaryl groups which may contain, for example, at least 8 carbon atoms, or mixtures thereof, and
quaternized hydroxyethylcelluloses modified with groups comprising at least one fatty chain, such as alkyl, arylalkyl or alkylaryl groups, which may contain, for example, at least 8 carbon atoms, or mixtures thereof.

In at least one embodiment of the present disclosure, the alkyl radicals borne by the above quaternized celluloses or hydroxyethylcelluloses contain from 8 to 30 carbon atoms. The aryl radicals may be chosen from phenyl, benzyl, naphthyl or anthryl groups.

Examples of quaternized alkylhydroxyethylcelluloses containing $C_8-C_{30}$ fatty chains that may be mentioned include the products Quatrisoft LM 200, Quatrisoft LM-X 529-18-A, Quatrisoft LM-X 529-18B ($C_{12}$ alkyl) and Quatrisoft LM-X 529-8 ($C_{18}$ alkyl) sold by the company Amerchol, and the products Crodacel QM, Crodacel QL ($C_{12}$ alkyl) and Crodacel QS ($C_{18}$ alkyl) sold by the company Croda.

Cationic Polyurethanes

According to at least one embodiment of the present disclosure, the cationic associative polyurethanes that may be used are chosen from those of the general formula (Ia):

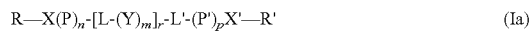

R—X(P)$_n$-[L-(Y)$_m$]$_r$-L'-(P')$_p$X'—R'  (Ia)

wherein:
R and R', which may be identical or different, are chosen from hydrophobic groups and hydrogen atoms;
X and X', which may be identical or different, are chosen from groups comprising an amine functional group optionally bearing a hydrophobic group, or alternatively a group L";
L, L' and L", which may be identical or different, are chosen from groups derived from a diisocyanate;
P and P', which may be identical or different, are chosen from groups comprising an amine functional group optionally bearing a hydrophobic group;

Y is chosen from hydrophilic groups;

r is an integer ranging from 1 to 100, such as, for example from 1 to 50 or from 1 to 25; and n, m and p each range, independently of each other, from 0 to 1,000;

wherein the molecule contains at least one protonated or quaternized amine functional group and at least one hydrophobic group.

These compounds have been described, for example, in European Patent Application No. EP 1 174 450.

In at least one embodiment, the only hydrophobic groups are the groups R and R' at the chain ends.

In at least one other embodiment, the cationic amphiphilic polyurethanes are chosen from those corresponding to formula (Ia) described above and in which:

R and R' are both independently chosen from hydrophobic groups,

X and X' are chosen from groups L", n and p range from 1 to 1,000, and

L, L', L", P, P', Y and m have the meaning given above.

In at least one embodiment of the present disclosure, the cationic amphiphilic polyurethanes are chosen from those of formula (Ia) above in which:

R and R' are both independently chosen from hydrophobic groups,

X and X' each are chosen from groups L", n and p are equal to zero, and

L, L', L", Y and m have the meaning given above.

When n and p are equal to zero, these polymers do not comprise units derived from a monomer containing an amine functional group, incorporated into the polymer during the polycondensation. The protonated amine functional groups of these polyurethanes result from the hydrolysis of excess isocyanate functional groups, at the chain end, followed by alkylation of the primary amine functional groups formed with alkylating agents containing a hydrophobic group, i.e., compounds of the type RQ or R'Q, wherein R and R' are as defined above and Q is chosen from leaving groups, such as a halide, a sulfate, etc.

In at least one embodiment, the cationic amphiphilic polyurethanes are chosen from those of formula (Ia) above in which:

R and R' are both independently chosen from hydrophobic groups,

X and X' are both independently chosen from groups comprising a quaternary amine, n and p are zero, and L, L', Y and m have the meaning given above.

In at least one embodiment, the number-average molecular mass of the cationic amphiphilic polyurethanes ranges from 400 to 500,000, such as, for example, from 1,000 to 400,000 or from 1,000 to 300,000.

As used herein, the expression "hydrophobic group" is understood to mean a radical or polymer containing a saturated or unsaturated, linear or branched hydrocarbon-based chain, which may contain at least one hetero atom such as P, O, N or S, or a radical containing a perfluoro or silicone chain. When the hydrophobic group denotes a hydrocarbon-based radical, it comprises at least 10 carbon atoms, such as from 10 to 30 carbon atoms, from 12 to 30 carbon atoms or from 18 to 30 carbon atoms.

In at least one embodiment, the hydrocarbon-based group is derived from a monofunctional compound.

By way of example, the hydrophobic group may be derived from a fatty alcohol such as stearyl alcohol, dodecyl alcohol or decyl alcohol. It may also denote a hydrocarbon-based polymer, for instance polybutadiene.

When X and/or X' are chosen from groups comprising a tertiary or quaternary amine, X and/or X' can be chosen from groups of one of the following formulae:

for X $$-\underset{R_1}{\underset{|}{N}}-R_2-\quad -\underset{R_1}{\overset{R_3}{\underset{|}{N^+}}}-R_2-\quad -R_2-\underset{R_1}{\overset{}{\underset{\diagdown}{N}}}\diagup R_1 \quad \text{or}$$

$$-R_2-\underset{R_1}{\overset{R_1}{\underset{|}{N^+}}}\diagdown R_1 \quad A^-$$

for X'

$$-R_2-\underset{R_1}{\underset{|}{N}}-\quad -R_2-\underset{R_1}{\overset{R_3}{\underset{|}{N^+}}}-\quad -R_2-\underset{R_1}{\overset{}{\underset{\diagdown}{N}}}\diagup R_1 \quad \text{or}$$

$$-R_2-\underset{R_1}{\overset{R_1}{\underset{|}{N^+}}}\diagdown R_1 \quad A^-$$

wherein:

$R_2$ is chosen from linear and branched alkylene radicals containing from 1 to 20 carbon atoms, optionally comprising a saturated or unsaturated ring, or an arylene radical, at least one carbon atom possibly being replaced with a hetero atom chosen from N, S, O and P;

$R_1$ and $R_3$, which may be identical or different, are chosen from linear and branched $C_1$-$C_{30}$ alkyl and alkenyl radicals and aryl radicals, at least one of the carbon atoms possibly being replaced with a hetero atom chosen from N, S, O and P; and $A^-$ is a physiologically acceptable counterion.

The groups L, L' and L" are chosen from groups of formula:

$$-Z-\underset{O}{\overset{\|}{C}}-NH-R_4-NH-\underset{O}{\overset{\|}{C}}-Z-$$

wherein:

Z is chosen from —O—, —S— and —NH—; and $R_4$ is chosen from linear and branched alkylene radicals containing from 1 to 20 carbon atoms, optionally comprising a saturated or unsaturated ring, or an arylene radical, at least one of the carbon atoms possibly being replaced with a hetero atom chosen from N, S, O and P.

The groups P and P' comprising an amine functional group may be chosen from at least one of the following formulae:

$$-R_5-\underset{R_6}{\underset{|}{N}}-R_7-\quad \text{or} \quad -R_5-\underset{R_6}{\overset{R_8}{\underset{|}{N^+}}}-R_7-\quad A^- \quad \text{or}$$

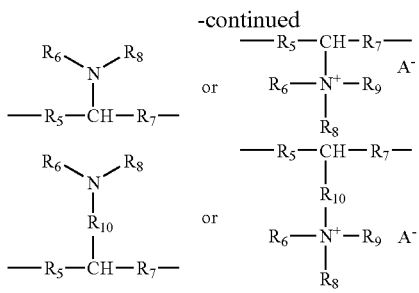

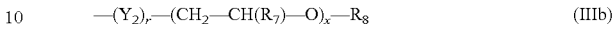

wherein:

$R_5$ and $R_7$ have the same meanings as $R_2$ defined above;

$R_6$, $R_8$ and $R_9$ have the same meanings as $R_1$ and $R_3$ defined above;

$R_{10}$ is chosen from linear and branched, optionally unsaturated alkylene groups possibly containing at least one hetero atom chosen from N, O, S and P; and $A^-$ is a physiologically acceptable counterion.

With regard to the meaning of Y, the term "hydrophilic group" is understood to mean a polymeric or nonpolymeric water-soluble group.

By way of example, when it is not a polymer, mention may be made of ethylene glycol, diethylene glycol and propylene glycol.

When it is a hydrophilic polymer, in accordance with at least one embodiment of the present disclosure, non-limiting mention may be made, for example, of polyethers, sulfonated polyesters, sulfonated polyamides or a mixture of these polymers. In at least one embodiment, the hydrophilic compound is a polyether, such as, for example, a poly(ethylene oxide) or poly(propylene oxide).

The hydrophilic group noted Y in formula (Ia) is optional. The units containing a protonated or quaternary amine functional group may suffice to provide the solubility or the water-dispersibility required for this type of polymer in an aqueous solution.

Although the presence of a hydrophilic group Y is optional, cationic amphiphilic polyurethanes comprising such a group are used in at least one embodiment of the present disclosure.

The cationic amphiphilic polyurethanes are water-soluble or water-dispersible.

Cationic Polyvinyllactams

The associative cationic poly(vinyllactam)polymers that may be used in the context of the present disclosure comprise:

a) at least one monomer of vinyllactam or alkylvinyllactam type;

b) at least one monomer chosen from those of formulae (Ib) and (IIb):

wherein:

X is chosen from oxygen atoms and radicals $NR_6$, $R_1$ and $R_6$ are chosen from, independently of each other, hydrogen atoms and linear and branched $C_1$-$C_5$ alkyl radicals, $R_2$ is chosen from linear and branched $C_1$-$C_4$ alkyl radicals, $R_3$, $R_4$ and $R_5$ are chosen from, independently of each other, hydrogen atoms, linear and branched $C_1$-$C_{30}$ alkyl radicals and radicals of formula (IIIb):

$$-(Y_2)_r-(CH_2-CH(R_7)-O)_x-R_8 \quad \text{(IIIb)}$$

Y, $Y_1$ and $Y_2$ are chosen from, independently of each other, linear and branched $C_2$-$C_{16}$ alkylene radicals, $R_7$ is chosen from hydrogen atoms, linear and branched $C_1$-$C_4$ alkyl radicals, and linear and branched $C_1$-$C_4$ hydroxyalkyl radicals, $R_8$ is chosen from hydrogen atoms and linear and branched $C_1$-$C_{30}$ alkyl radicals, p, q and r are, independently of each other, either the value 0 or the value 1, m and n are, independently of each other, integers ranging from 0 to 100, x is an integer ranging from 1 to 100, and Z is chosen from organic and mineral acid anions, with the proviso that:

at least one of the substituents $R_3$, $R_4$, $R_5$ or $R_8$ is chosen from linear and branched $C_8$-$C_{30}$ alkyl radicals, such as, for example, $C_9$-$C_{30}$ alkyl radicals, if m or n is other than zero, then q is equal to 1, if m or n is equal to zero, then p or q is equal to 0.

The associative cationic poly(vinyllactam) polymers that may be used according to the present disclosure may be crosslinked or noncrosslinked and may also be block polymers.

In at least one embodiment, the counterion $Z^-$ of the monomers of formula (Ib) is chosen from halide ions, phosphate ions, methosulfate ions and tosylate ions.

In at least one embodiment, $R_3$, $R_4$ and $R_5$ are chosen from, independently of each other, hydrogen atoms and linear and branched $C_1$-$C_{30}$ alkyl radicals.

In at least one embodiment, a monomer of formula (Ib) for which m and n are equal to 0, is used.

In at least one embodiment, the vinyllactam or alkylvinyllactam monomer is chosen from compounds of formula (IVb):

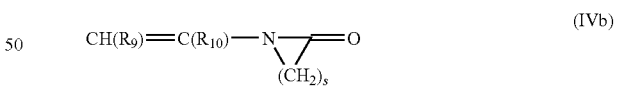

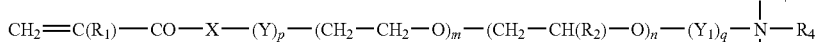

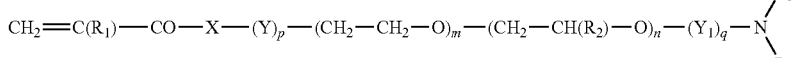

wherein:

s is an integer ranging from 3 to 6, $R_9$ is chosen from hydrogen atoms and $C_1$-$C_5$ alkyl radicals, and $R_{10}$ is chosen from hydrogen atoms and $C_1$-$C_5$ alkyl radicals, with the proviso that at least one of the radicals $R_9$ and $R_{10}$ is a hydrogen atom.

In at least one embodiment, the monomer (IVb) is vinylpyrrolidone.

The cationic poly(vinyllactam)polymers may also contain at least one additional monomer, such as, for example, cationic or nonionic monomers.

Among compounds that may be used according to at least one embodiment of the disclosure, non-limiting mention may be made of the following terpolymers comprising at least:

(a) one monomer of formula (IVb), (b) one monomer of formula (Ib) wherein p=1, q=0, $R_3$ and $R_4$ are chosen from, independently of each other, hydrogen atoms and $C_1$-$C_5$ alkyl radicals, and $R_5$ is chosen from $C_8$-$C_{24}$ alkyl radicals, such as, for example, $C_9$-$C_{24}$ alkyl radicals, and (c) one monomer of formula (IIb) wherein $R_3$ and $R_4$ are chosen from, independently of each other, hydrogen atoms and $C_1$-$C_5$ alkyl radicals.

In at least one embodiment, terpolymers comprising, by weight, 40% to 95% of monomer (a), 0.1% to 55% of monomer (c), and 0.25% to 50% of monomer (b) will be used.

Such polymers are described in International Patent Application No. WO 00/68282, the content of which is incorporated herein by reference.

Among cationic poly(vinyllactam)polymers according to at least one embodiment of the present disclosure, non-limiting mention may be made of vinylpyrrolidone/dimethylaminopropylmethacrylamide/dodecyldimethylmethacrylamidopropylammonium tosylate terpolymers, vinylpyrrolidone/dimethylaminopropylmethacrylamide/cocoyldimethylmethacrylamidopropylammonium tosylate terpolymers, vinylpyrrolidone/dimethylaminopropylmethacrylamide/lauryldimethylmethacrylamidopropylammonium tosylate or chloride terpolymers.

The weight-average molecular mass of the cationic associative poly(vinyllactam)polymers according to the present disclosure can range from 500 to $20 \times 10^6$. For example, the weight-average molecular mass of the cationic associative poly(vinyllactam)polymers may range from 200,000 to $2 \times 10^6$ of from 400,000 to 800,000.

Acrylic Terpolymers

Among these polymers, non-limiting mention may be made of acrylic terpolymers comprising:

from 5% to 80% by weight, such as from 15% to 70% by weight or from 40% to 70% by weight of an acrylate monomer (a) chosen from $C_1$-$C_6$ alkyl acrylates and $C_1$-$C_6$ alkyl methacrylates;

from 5% to 80% by weight, such as from 10% to 70% by weight or from 20% to 60% by weight, of a monomer (b) chosen from heterocyclic vinyl compounds containing at least one nitrogen or sulfur atom, (meth)acrylamides, mono- or di($C_1$-$C_4$)alkylamino($C_1$-$C_4$)alkyl(meth)acrylates and mono- or di($C_1$-$C_4$)alkylamino($C_1$-$C_4$)alkyl(meth)acrylamides;

from 0.1% to 30% by weight, such as from 0.1% to 10% by weight, of a monomer (c) chosen from: (i) urethanes produced by reaction between a monoethylenic unsaturated isocyanate and a nonionic surfactant with a $C_1$-$C_4$ alkoxy end; (ii) block copolymers of 1,2-butylene oxide and of 1,2-ethylene oxide; (iii) copolymerizable ethylenic unsaturated surfactant monomers obtained by condensation of a nonionic surfactant with an α,β-ethylenic unsaturated carboxylic acid or its anhydride; (iv) surfactant monomers chosen from the products of reaction such as a urea of a monoethylenic unsaturated monoisocyanate with a nonionic surfactant containing an amine functional group; (v) (meth)allyl ethers of formula $CH_2=CR_1CH_2OA_mB_nA_pR_2$ wherein $R_1$ is chosen from hydrogen atoms and methyl groups, A is chosen from propyleneoxy and butyleneoxy groups, B is ethyleneoxy, n is equal to zero or an integer less than or equal to 200, such as less than 100, m and p are zero or an integer less than n, and $R_2$ is chosen from hydrophobic groups of at least 8 carbon atoms, such as $C_8$-$C_{30}$; and (vi) nonionic monomers of urethane type produced by reaction of a monohydric nonionic surfactant with a monoethylenic unsaturated isocyanate; wherein the weight percentages of monomers is based on the total weight of the monomers constituting the terpolymer.

Acrylate monomers (a) that may be used in at least one embodiment comprise $C_2$-$C_6$ alkyl acrylates. In at least one embodiment, for example, ethyl acrylate is used.

Examples of monomers (b) which may be mentioned include N,N-dimethylaminoethyl methacrylate (DMAEMA), N,N-diethylaminoethyl acrylate, N,N-diethylaminoethyl methacrylate, N-t-butylaminoethyl acrylate, N-t-butylaminoethyl methacrylate, N,N-dimethylamino-propylacrylamide, N,N-dimethylaminopropylmethacrylamide, N,N-diethylaminopropylacrylamide and N,N-diethylaminopropylmethacrylamide. For instance, N,N-dimethylaminoethyl methacrylate is used in at least one embodiment.

In at least one other embodiment, the monomers (c) are chosen from the copolymerizable ethylenic unsaturated surfactant monomers obtained by condensing a nonionic surfactant with an α,β-ethylenic unsaturated carboxylic acid or its anhydride, such as $C_3$-$C_4$ mono- or dicarboxylic acids or their anhydrides and, in at least one other embodiment, acrylic acid, methacrylic acid, crotonic acid, maleic acid, and maleic anhydride, and in at least one further embodiment, itaconic acid and itaconic anhydride.

The monomers (c) that may be used in at least one embodiment correspond to the copolymerizable ethylenic unsaturated surfactant monomers obtained by condensing a nonionic surfactant with itaconic acid. Among the nonionic surfactants which may be used according to at least one embodiment of the present disclosure, non-limiting mention may be made of $C_{10}$-$C_{30}$ fatty alcohols alkoxylated with 2 to 100 mol, such as, for example, from 5 to 50 mol of an alkylene oxide, for instance polyethylene glycol ethers of $C_{10}$-$C_{30}$ fatty alcohols and, in at least one further embodiment, the polyethylene glycol ethers of cetyl alcohol, which are known as Ceteth in the CTFA dictionary, 7th edition, 1997.

Conventional methods for preparing these acrylic terpolymers are known to those skilled in the art. Such methods include solution polymerization, precipitation polymerization and emulsion polymerization. Terpolymers in accordance with the present disclosure and methods for preparing them are described, for example, in European Patent Application Nos. EP-A-0 824 914 and EP-A-0 825 200.

Among these terpolymers, at least one embodiment of the present disclosure uses the "Structure® Plus" polymer sold by the company National Starch, which comprises acrylates, amino(meth)acrylates and $C_{10}$-$C_{30}$ alkyl itaconate, polyoxyethylenated with 20 mol of ethylene oxide, in the form of an aqueous dispersion containing 20% Active Material.

In addition to these monomers, the terpolymers can contain other monomers that allow the terpolymers to be crosslinked. These monomers may be used in relatively low amounts, of up to 2% by weight relative to the total weight of the monomers used to prepare the terpolymers. Such crosslinking monomers may comprise aromatic monomers bearing several vinyl substituents, alicyclic monomers bearing several vinyl substituents, bifunctional esters of phthalic acid, bifunctional esters of methacrylic acid, multifunctional esters of acrylic acid, N-methylenebisacrylamide and aliphatic monomers bearing several vinyl substituents such as dienes, trienes and tetraenes.

Crosslinking monomers may include, for example, divinylbenzenes, trivinylbenzenes, 1,2,4-trivinylcyclohexene, 1,5-hexadiene, 1,5,9-decatriene, 1,9-decadiene, 1,5-heptadiene, diallyl phthalates, ethylene glycol dimethacrylate, polyethylene glycol dimethacrylates, penta- and tetraacrylates, triallyl pentaerythritols, octaallyl sucroses, cycloparaffins, cycloolefins and N-methylenebisacrylamide.

In at least one embodiment of the present disclosure, the at least one cationic associative polymer may be used in an amount that can range from 0.01% to 5% by weight, relative to the weight of the dye composition. For example, the at least one cationic associative polymer may be used in an amount ranging from 0.05% to 2.5% by weight, relative to the weight of the dye composition. In accordance with at least one embodiment, the at least one cationic associative polymer is present in an amount ranging from 0.1% to 1% by weight, relative to the weight of the dye composition.

The composition according to the disclosure also comprises at least one dye chosen from oxidation dye precursors and direct dyes.

The at least one oxidation dye precursor can be chosen from oxidation bases and couplers.

The at least one oxidation base can be chosen from the oxidation bases conventionally used for oxidation dyeing, among which non-limiting mention may be made of para-phenylenediamines, bis(phenyl)alkylenediamines, para-aminophenols, ortho-aminophenols and heterocyclic bases, and the addition salts thereof with an acid or with an alkaline agent.

Among the para-phenylenediamines that may be used according to at least one embodiment, non-limiting mention may be made of, for example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4'-aminophenyl-1-(3-hydroxy)pyrrolidine, and the addition salts thereof with an acid or with an alkaline agent.

Among the para-phenylenediamines mentioned above, at least one embodiment of the present disclosure uses those chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid or with an alkaline agent.

Among the bis(phenyl)alkylenediamines that may be used according to the present disclosure, non-limiting mention may be made of, for example, N,N'-bis(β-hydroxyethyl)-N, N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid or with an alkaline agent.

Among the para-aminophenols that may be used according to the disclosure, non-limiting mention may be made of, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid or with an alkaline agent.

Among the ortho-aminophenols that may be used according to the present disclosure, non-limiting mention may be made of, for example, 2-aminophenol, 2-amino-5-methylphenol, 2-amino-6-methylphenol and 5-acetamido-2-aminophenol, and the addition salts thereof with an acid or with an alkaline agent.

Among the heterocyclic bases that may be used according to the present disclosure, non-limiting mention may be made of, for example, pyridine derivatives, such as 2,3-diamino-6-methoxypyridine; pyrimidine derivatives such as, for example, 2,4,5,6-tetraaminopyrimidine or 4-hydroxy-2,5,6-triaminopyrimidine; and pyrazole derivatives, for instance 1N-β-hydroxyethyl-4,5-diaminopyrazole; and the addition salts thereof with an acid or with an alkaline agent.

When they are used, the at least one oxidation base may be present in an amount ranging from 0.0005% to 12% by weight relative to the weight of the dye composition, such as, for example, from 0.005% to 6% by weight relative to the weight of the dye composition.

The composition may also comprise, combined with at least one oxidation base, at least one coupler so as to modify or to enrich with tints the shades obtained.

The at least one coupler that may be used may be chosen from the couplers conventionally used in oxidation dyeing, and among which non-limiting mention may be made of meta-phenylenediamines, meta-aminophenols, meta-diphenols and heterocyclic couplers, and the addition salts thereof with an acid or with an alkaline agent.

In at least one embodiment of the present disclosure, the at least one coupler may be chosen from 2-methyl-5-aminophenol, 5-N-(β-hydroxyethyl)amino-2-methylphenol, 3-aminophenol, 2-methyl-5-amino-6-chlorophenol, 1,3-dihydroxybenzene, 1,3-dihydroxy-2-methylbenzene, 4-chloro-1, 3-dihydroxybenzene, 2,4-diamino-1-(β-hydroxyethyloxy)benzene, 2-amino-4-(β-hydroxyethylamino)-1- methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2-amino-3-hydroxypyridine, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, and the addition salts thereof with an acid or with an alkaline agent.

When present, the at least one coupler may be present in an amount ranging from 0.0001% to 15% by weight, such as, for example, from 0.005% to 12% by weight relative to the weight of the dye composition. In accordance with at least one embodiment, the at least one coupler is present in an amount ranging from 0.01% to 10% by weight relative to the total weight of the dye composition.

In at least one embodiment, the addition salts with an acid may be chosen from the hydrochlorides, hydrobromides, sulfates, citrates, succinates, tartrates, tosylates, benzenesulfonates, lactates and acetates.

In at least one other embodiment, the at least one direct dye is chosen from those of nonionic, cationic and anionic nature. Non-limiting examples that may be mentioned include nitrobenzene dyes, azo, azomethine, methine, tetraazapentamethine, anthraquinone, naphthoquinone, benzoquinone, phenothiazine, indigoid, xanthene, phenanthridine, phthalocyanin and triarylmethane-based dyes and natural dyes, alone or as mixtures.

The at least one direct dye may be chosen, for example, from the following red or orange nitrobenzene dyes:
   1-hydroxy-3-nitro-4-N-(γ-hydroxypropyl)aminobenzene,
   N-(β-hydroxyethyl)amino-3-nitro-4-aminobenzene,
   1-amino-3-methyl-4-N-(β-hydroxyethyl)amino-6-nitrobenzene,
   1-hydroxy-3-nitro-4-N-(β-hydroxyethyl)aminobenzene,
   1,4-diamino-2-nitrobenzene,
   1-amino-2-nitro-4-methylaminobenzene,
   N-(β-hydroxyethyl)-2-nitro-para-phenylenediamine,
   1-amino-2-nitro-4-(β-hydroxyethyl)amino-5-chlorobenzene,
   2-nitro-4-aminodiphenylamine,
   1-amino-3-nitro-6-hydroxybenzene,
   1-(β-aminoethyl)amino-2-nitro-4-(β-hydroxyethyloxy)benzene,
   1-(β,γ-dihydroxypropyl)oxy-3-nitro-4-(β-hydroxyethyl)aminobenzene,
   1-hydroxy-3-nitro-4-aminobenzene,
   1-hydroxy-2-amino-4,6-dinitrobenzene,
   1-methoxy-3-nitro-4-(β-hydroxyethyl)aminobenzene,
   2-nitro-4'-hydroxydiphenylamine, and
   1-amino-2-nitro-4-hydroxy-5-methylbenzene.

The at least one direct dye may also be chosen from yellow and green-yellow nitrobenzene direct dyes. Non-limiting mention may be made, for example, of the compounds chosen from:
   1-β-hydroxyethyloxy-3-methylamino-4-nitrobenzene,
   1-methylamino-2-nitro-5-(β,γ-dihydroxypropyl)oxybenzene,
   1-(β-hydroxyethyl)amino-2-methoxy-4-nitrobenzene,
   1-(β-aminoethyl)amino-2-nitro-5-methoxybenzene,
   1,3-di(β-hydroxyethyl)amino-4-nitro-6-chlorobenzene,
   1-amino-2-nitro-6-methylbenzene,
   1-(β-hydroxyethyl)amino-2-hydroxy-4-nitrobenzene,
   N-(β-hydroxyethyl)-2-nitro-4-trifluoromethylaniline,
   4-(β-hydroxyethyl)amino-3-nitrobenzenesulfonic acid,
   4-ethylamino-3-nitrobenzoic acid,
   4-(β-hydroxyethyl)amino-3-nitrochlorobenzene,
   4-(β-hydroxyethyl)amino-3-nitromethylbenzene,
   4-(β,γ-dihydroxypropyl)amino-3-nitrotrifluoromethylbenzene,
   1-(β-ureidoethyl)amino-4-nitrobenzene,
   1,3-diamino-4-nitrobenzene,
   1-hydroxy-2-amino-5-nitrobenzene,
   1-amino-2-[tris(hydroxymethyl)methyl]amino-5-nitrobenzene,
   1-(β-hydroxyethyl)amino-2-nitrobenzene, and
   4-(β-hydroxyethyl)amino-3-nitrobenzamide.

Non-limiting mention may also be made of blue or violet nitrobenzene direct dyes, for instance:
   1-(β-hydroxyethyl)amino-4-N,N-bis(β-hydroxyethyl)amino-2-nitrobenzene,
   1-(γ-hydroxypropyl)amino-4, N,N-bis(β-hydroxyethyl)amino-2-nitrobenzene,
   1-(β-hydroxyethyl)amino-4-(N-methyl-N-β-hydroxyethyl)amino-2-nitrobenzene,
   1-(β-hydroxyethyl)amino-4-(N-ethyl-N-β-hydroxyethyl)amino-2-nitrobenzene,
   1-(β,γ-dihydroxypropyl)amino-4-(N-ethyl-N-β-hydroxyethyl)amino-2-nitrobenzene, and
   2-nitro-para-phenylenediamines having the following formula:

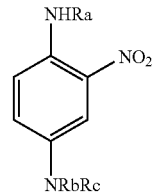

wherein:
   Rb is chosen from $C_1$-$C_4$ alkyl radicals, β-hydroxyethyl radicals, β-hydroxypropyl radicals, and γ-hydroxypropyl radicals;
   Ra and Rc, which may be identical or different, are chosen from β-hydroxyethyl, β-hydroxypropyl, γ-hydroxypropyl and β,γ-dihydroxypropyl radicals, at least one of the radicals Rb, Rc or Ra being chosen from y-hydroxypropyl radicals and with the proviso that Ra and Rc are not simultaneously chosen from β-hydroxyethyl radicals when Rb is a δ-hydroxypropyl radical, such as those described in French Patent No. FR 2 692 572.

Among the azo direct dyes that may be used according to the disclosure, non-limiting mention may be made of the cationic azo dyes described in Patent Application Nos. WO 95/15144, WO 95/01772, EP 714 954, FR 2 822 696, FR 2 825 702, FR 2 825 625, FR 2 822 698, FR 2 822 693, FR 2 822 694, FR 2 829 926, FR 2 807 650, WO 02/078 660, WO 02/100 834, WO 02/100 369 and FR 2 844 269.

Among these compounds, non-limiting mention may be made of the following dyes:
   1,3-dimethyl-2-[[4-(dimethylamino)phenyl]azo]-1H-imidazolium chloride,
   1,3-dimethyl-2-[(4-aminophenyl)azo]-1H-imidazolium chloride, and
   1-methyl-4-[(methylphenylhydrazono)methyl]pyridinium methyl sulfate.

Among the azo direct dyes that may also be mentioned are the following dyes described in the Color Index International 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Non-limiting mention may also be made of 1-(4'-aminodiphenylazo)-2-methyl-4-[bis(β-hydroxyethyl)amino]benzene and 4-hydroxy-3-(2-methoxyphenylazo)-1-naphthalenesulfonic acid.

Among examples of the quinone direct dyes that may be mentioned are the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds:
- 1-N-methylmorpholiniumpropylamino-4-hydroxyanthraquinone,
- 1-aminopropylamino-4-methylaminoanthraquinone,
- 1-aminopropylaminoanthraquinone,
- 5-β-hydroxyethyl-1,4-diaminoanthraquinone,
- 2-aminoethylaminoanthraquinone, and
- 1,4-bis(β,γ-dihydroxypropylamino)anthraquinone.

Among examples of the azine dyes that may used according to the present disclosure, non-limiting mention may be made of Basic Blue 17 and Basic Red 2.

Among the cationic methine direct dyes, non-limiting mention may also be made of Basic Red 14, Basic Yellow 13 and Basic Yellow 29.

Among the triarylmethane dyes that may be used according to the present disclosure, non-limiting mention may be made of the following compounds: Basic Green 1, Acid Blue 9, Basic Violet 3, Basic Violet 14, Basic Blue 7, Acid Violet 49, Basic Blue 26, and Acid Blue 7.

Among the indoamine dyes that may be used according to the present disclosure, non-limiting mention may be made of the following compounds:
- 2-β-hydroxyethylamino-5-[bis(β-4'-hydroxyethyl)amino] anilino-1,4-benzoquinone;
- 2-β-hydroxyethylamino-5-(2'-methoxy-4'-amino)anilino-1,4-benzoquinone;
- 3-N(2'-chloro-4'-hydroxy)phenylacetylamino-6-methoxy-1,4-benzoquinoneimine;
- 3-N(3'-chloro-4'-methylamino)phenylureido-6-methyl-1,4-benzoquinoneimine; and
- 3-[4'-N-(ethylcarbamylmethyl)amino]phenylureido-6-methyl-1,4-benzoquinoneimine.

The composition may also comprise natural direct dyes, for instance lawsone, juglone, alizarin, purpurin, carminic acid, kermesic acid, purpurogallin, protocatechaldehyde, indigo, isatin, curcumin, spinulosin or apigenidin. Extracts or decoctions containing these natural dyes, such as, for example, henna-based poultices or extracts, may also be used.

The at least one direct dye, when present, may be present in an amount ranging from 0.0005% to 15% by weight relative to the weight of the dye composition, such as, for example, from 0.005% to 12% by weight relative to the weight of the dye composition. According to at least one embodiment of the present disclosure, the at least one direct dye is present in an amount ranging from 0.01% to 5% by weight relative to the weight of the dye composition.

The composition according to the disclosure may also comprise at least one basifying agent.

Among basifying agents that may be mentioned, for example, are aqueous ammonia, alkali metal carbonates, $C_2$-$C_{10}$ alkanolamines such as monoethanolamine, diethanolamine and triethanolamine and also derivatives thereof, oxyethylenated and/or oxypropylenated hydroxyalkylamines and ethylenediamines, sodium hydroxide, potassium hydroxide, alkali metal or alkaline-earth metal silicates and the compounds having the following formula:

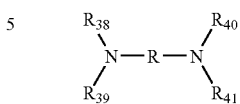

wherein R is a propylene residue optionally substituted with a hydroxyl group or a $C_1$-$C_4$ alkyl radical; $R_{38}$, $R_{39}$, $R_{40}$ and $R_{41}$, which may be identical or different, are chosen from hydrogen atoms, $C_1$-$C_4$ alkyl radicals, and $C_1$-$C_4$ hydroxyalkyl radicals.

In at least one embodiment, the at least one basifying agent is chosen from aqueous ammonia, alkanolamines and combinations of alkanolamines with alkali metal or alkaline-earth metal silicates.

According to at least one embodiment of the present disclosure, the composition does not comprise aqueous ammonia as basifying agent.

It should moreover be noted that the pH may also be adjusted by using acidifying agents, for instance mineral or organic acids such as hydrochloric acid, orthophosphoric acid or sulfuric acid, carboxylic acids, for instance acetic acid, tartaric acid, citric acid or lactic acid, or sulfonic acids.

In at least one embodiment, the amount of basifying and/or acidifying agent present is such that the pH of the dye composition ranges from 3 to 12, such as, for example, from 4 to 11 or from 7 to 11.

The composition according to the disclosure may also comprise at least one cationic or amphoteric substantive polymer.

It should be noted that, for the purposes of the present disclosure, the term "cationic polymer" is understood to mean any polymer containing cationic groups and/or groups that may be ionized into cationic groups.

Such polymers may be chosen from those already known per se as improving the cosmetic properties of the hair, such as, for example, those described in European Patent Application No. EP-A-337 354 and in French Patent Nos. FR 2 270 846, FR 2 383 660, FR 2 598 611, FR 2 470 596, and FR 2 519 863.

The cationic polymers that may be used according to at least one embodiment are chosen from those containing units comprising primary, secondary, tertiary and/or quaternary amine groups, which may either form part of the main polymer chain or may be borne by a side substituent directly attached thereto.

The cationic polymers used may generally have a number-average molecular mass ranging from 500 to $5 \times 10^6$, such as from $10^3$ to $3 \times 10^6$.

Among the cationic polymers that may be used according to at least one embodiment, non-limiting mention may be made of polymers of the polyamine, polyamino amide and polyquaternary ammonium type.

These are known products. They are described, for example, in French Patent Nos. FR 2 505 348 and FR 2 542 997. Among the polymers, further non-limiting mention may be made of:

(1) homopolymers or copolymers derived from acrylic or methacrylic esters or amides and comprising at least one unit chosen from those of formulae (I), (II), (III) and (IV):

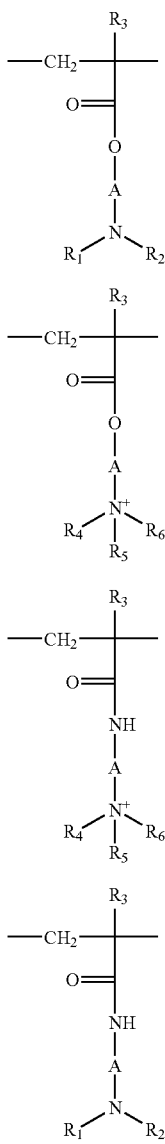

wherein:

$R_3$, which may be identical or different, is chosen from hydrogen atoms and $CH_3$ radicals;

A, which may be identical or different, is chosen from linear and branched alkyl groups of 1 to 6 carbon atoms, such as, for example, 2 or 3 carbon atoms, and hydroxyalkyl groups of 1 to 4 carbon atoms;

$R_4$, $R_5$ and $R_6$, which may be identical or different, are chosen from alkyl groups containing from 1 to 18 carbon atoms, benzyl radicals, and in at least one embodiment, alkyl groups containing from 1 to 6 carbon atoms;

$R_1$ and $R_2$, which may be identical or different, are chosen from hydrogen atoms and alkyl groups containing from 1 to 6 carbon atoms, such as, for example, methyl or ethyl; and X is chosen from anions derived from an inorganic or organic acid, such as a methosulfate anion, and halides such as chloride or bromide.

The polymers of family (1) can also contain at least one unit derived from comonomers which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Thus, among these polymers of family (1), further non-limiting mention may be made of:

copolymers of acrylamide and of dimethylaminoethyl methacrylate quaternized with dimethyl sulfate or with a dimethyl halide, such as the product sold under the name Hercofloc by the company Hercules, the copolymers of acrylamide and of methacryloyloxyethyltrimethylammonium chloride described, for example, in European Patent Application No. EP-A-080 976 and sold under the name Bina Quat P 100 by the company Ciba Geigy, the copolymer of acrylamide and of methacryloyloxyethyltrimethylammonium methosulfate sold under the name Reten by the company Hercules, quaternized or non-quaternized vinylpyrrolidone/dialkylaminoalkyl acrylate or methacrylate copolymers, such as the products sold under the name "Gafquat" by the company ISP, for instance "Gafquat 734" or "Gafquat 755," or alternatively the products known as "Copolymer 845, 958 and 937." These polymers are described in detail in French Patent Nos. FR 2 077 143 and FR 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold, for example, under the name Styleze CC 10 by ISP, and quaternized vinylpyrrolidone/dimethylaminopropyl methacrylamide copolymers such as the product sold under the name "Gafquat HS 100" by the company ISP.

(2) The cellulose ether derivatives comprising quaternary ammonium groups, which are described in French Patent No. FR 1 492 597, and, for example, the polymers sold under the names "JR" (JR 400, JR 125, JR 30M) or "LR" (LR 400, LR 30M) by the company Union Carbide Corporation. These polymers are also defined in the CTFA dictionary as hydroxyethylcellulose quaternary ammoniums that have reacted with an epoxide substituted with a trimethylammonium group.

(3) Cationic cellulose derivatives such as the copolymers of cellulose or cellulose derivatives grafted with a water-soluble quaternary ammonium monomer, described, for example, in U.S. Pat. No. 4,131,576, such as hydroxyalkylcelluloses, for instance hydroxymethyl-, hydroxyethyl- or hydroxypropylcelluloses grafted, for example, with a methacryloylethyltrimethylammonium, methacrylamidopropyltrimethylammonium or dimethyldiallylammonium salt.

The commercial products corresponding to this definition include the products sold under the name Celquat L 200 and Celquat H 100 by the company National Starch.

(4) The cationic guar gums described in U.S. Pat. Nos. 3,589, 578 and 4,031,307, such as guar gums containing trialkylammonium cationic groups. Use may be made, for example, of guar gums modified with a salt (e.g. chloride) of 2,3-epoxypropyltrimethylammonium.

Such products are sold for instance under the trade names Jaguar C13S, Jaguar C15, Jaguar C17 and Jaguar C162 by the company Meyhall.

(5) Polymers comprising piperazinyl units and divalent alkylene or hydroxyalkylene radicals containing straight or branched chains, optionally interrupted by oxygen, sulfur or nitrogen atoms or by aromatic or heterocyclic rings, and also the oxidation and/or quaternization products of these polymers. Such polymers are described, for example, in French Patent Nos. FR 2 162 025 and FR 2 280 361.

(6) Water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in an amount ranging from 0.025 mol to 0.35 mol per amine group of the polyamino amide; these polyamino amides can be alkylated or, if they contain at least one tertiary amine functional group, they can be quaternized. Such polymers are described, for example, in French Patent Nos. FR 2 252 840 and FR 2 368 508.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylene-triamine polymers in which the alkyl radical contains from 1 to 4 carbon atoms, such as, for example, methyl, ethyl or propyl. Such polymers are described in French Patent No. FR 1 583 363.

Among these derivatives, non-limiting mention may be made of the adipic acid/dimethylaminohydroxypropyl/diethylenetriamine polymers sold under the name "Cartaretine F, F4 or F8" by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid ranges from 0.8:1 to 1.4:1; the polyamino amide resulting therefrom is reacted with epichlorohydrin in a molar ratio of epichlorohydrin relative to the secondary amine group of the polyamino amide ranging from 0.5:1 to 1.8:1. Such polymers are described in U.S. Pat. Nos. 3,227, 615 and 2,961,347.

Polymers of this type are sold, for example, under the name "Hercosett 57" by the company Hercules Inc. or alternatively under the name "PD 170" or "Delsette 101" by the company Hercules in the case of the adipic acid/epoxypropyl/diethylenetriamine copolymer.

(9) Cyclopolymers of alkyldiallylamine or of dialkyldiallylammonium, such as the homopolymers or copolymers containing, as main constituent of the chain, units chosen from those of formulae (V) and (VI):

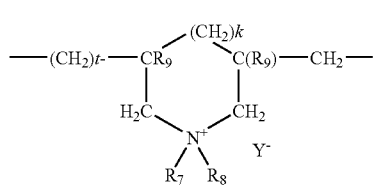

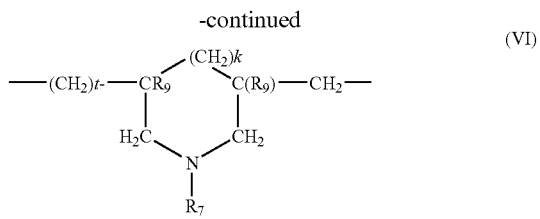

wherein
k and t are equal to 0 or 1, the sum k+t being equal to 1;
$R_9$ is chosen from hydrogen atoms and methyl radicals;
$R_7$ and $R_8$, independently of each other, are chosen from alkyl groups having from 1 to 6 carbon atoms, hydroxyalkyl groups in which the alkyl group comprises, for example, 1 to 5 carbon atoms, lower ($C_1$-$C_4$) amidoalkyl groups, or $R_7$ and $R_8$ can form, together with the nitrogen atom to which they are attached, heterocyclic groups such as piperidyl or morpholinyl; $R_7$ and $R_8$, independently of each other, in at least one embodiment, are chosen from alkyl groups having from 1 to 4 carbon atoms; and $Y^-$ is chosen from anions such as bromide, chloride, acetate, borate, citrate, tartrate, bisulfate, bisulfite, sulfate or phosphate.

These polymers are described, for example, in French Patent No. FR 2 080 759 and in its Certificate of Addition 2 190 406.

Among the polymers defined above, further non-limiting mention may be made of the dimethyldiallylammonium chloride homopolymer sold under the name "Merquat 100" by the company Calgon (and its homologues of low weight-average molecular mass) and the copolymers of diallyldimethylammonium chloride and of acrylamide, sold under the name "Merquat 550."

(10) The quaternary diammonium polymer containing repeating units of formula (VII):

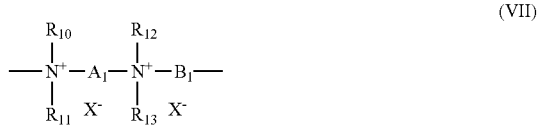

wherein:
$R_{10}$, $R_{11}$, $R_{12}$ and $R_{13}$, which may be identical or different, are chosen from aliphatic, alicyclic and arylaliphatic radicals containing from 1 to 20 carbon atoms and lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second hetero atom other than nitrogen, or alternatively $R_{10}$, $R_{11}$, $R_{12}$ and $R_{13}$ are chosen from linear and branched $C_1$-$C_6$ alkyl radicals substituted with a nitrile, ester, acyl or amide group or a group —CO—O—$R_{14}$-D or —CO—NH—$R_{14}$-D where $R_{14}$ is an alkylene and D is a quaternary ammonium group;

$A_1$ and $B_1$ are chosen from polymethylene groups containing from 2 to 20 carbon atoms which may be linear or branched, saturated or unsaturated, and which may contain, linked to or intercalated in the main chain, at least one aromatic ring or at least one oxygen or sulfur atom or sulfoxide, sulfone, disulfide, amino, alkylamino, hydroxyl, quaternary ammonium, ureido, amide or ester groups; and X⁻ is chosen from anions derived from an inorganic or organic acid;

$A_1$, $R_{10}$ and $R_{12}$ can form, with the two nitrogen atoms to which they are attached, a piperazine ring; in addition, if $A_1$ is chosen from linear and branched, saturated and unsaturated alkylene or hydroxyalkylene radicals, $B_1$ can also be chosen from groups $-(CH_2)_n-CO-D-OC-(CH_2)_n-$ wherein n ranges from 1 to 100, such as, for example, from 1 to 50, and D is chosen from:

a) a glycol residue of formula: $-O-Z-O-$, where Z is chosen from linear and branched hydrocarbon-based radicals or groups corresponding to one of the following formulae:

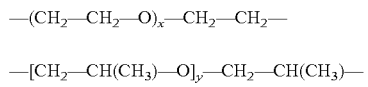

where x and y are integers from 1 to 4, representing a defined and unique degree of polymerization, or any number from 1 to 4 representing an average degree of polymerization;

b) a bis-secondary diamine residue such as a piperazine derivative;

c) a bis-primary diamine residue of formula: $-NH-Y-NH-$, where Y is chosen from linear and branched hydrocarbon-based radicals, or alternatively the divalent radical $-CH_2-CH_2-S-S-CH_2-CH_2-$;

d) ureylene groups of formula: $-NH-CO-NH-$.

In at least one embodiment, X⁻ is chosen from anions such as chloride or bromide.

These polymers may generally have a number-average molecular mass ranging from 1,000 to 100,000.

Polymers of this type are described, for example, in French Patent Nos. FR 2 320 330, FR 2 270 846, FR 2 316 271, FR 2 336 434 and FR 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

In at least one embodiment of the present disclosure, it is possible to use polymers that comprise repeating units chosen from those of formula (VIII):

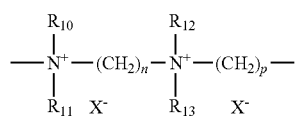

(VIII)

wherein $R_{10}$, $R_{11}$, $R_{12}$ and $R_{13}$, which may be identical or different, are chosen from alkyl and hydroxyalkyl radicals containing from 1 to 4 carbon atoms, n and p are integers ranging from 2 to 20, and X⁻ is an anion derived from a mineral or organic acid.

(11) Polyquaternary ammonium polymers comprising units of formula (IX)

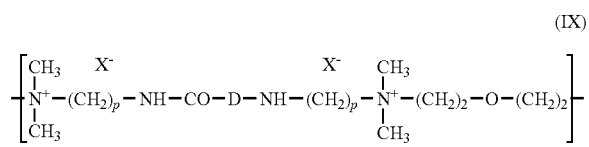

(IX)

wherein p is an integer ranging from 1 to 6, D may be nothing, or may be chosen from groups $-(CH_2)_r-CO-$ wherein r denotes a number equal to 4 or 7, and X⁻ is an anion.

Such polymers may be prepared according to the processes described in U.S. Pat. Nos. 4,157,388, 4,702,906 and 4,719,282. They are also described in European Patent Application No. EP-A-122 324.

Among these polymers, examples that may be mentioned include the products "Mirapol A 15," "Mirapol AD1," "Mirapol AZ1," and "Mirapol 175" sold by the company Miranol.

(12) Quaternary polymers of vinylpyrrolidone and of vinylimidazole, for instance the products sold under the names Luviquat FC 905, FC 550 and FC 370 by the company BASF.

(13) Polyamines such as Polyquart H sold by Henkel, which is given under the reference name "Polyethylene glycol (15) tallow polyamine" in the CTFA dictionary.

(14) Crosslinked methacryloyloxy($C_1$-$C_4$)alkyltri($C_1$-$C_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, such as methylenebisacrylamide. A crosslinked acrylamide/methacryloyloxyethyltrimethylammonium chloride copolymer (20/80 by weight) in the form of a dispersion containing 50% by weight of the copolymer in mineral oil can be used in at least one embodiment. This dispersion is sold under the name "Salcare® SC 92" by the company Allied Colloids. A crosslinked meth-acryloyloxyethyltrimethylammonium chloride homopolymer containing about 50% by weight of the homopolymer in mineral oil or in a liquid ester can also be used. These dispersions are sold under the names "Salcare® SC 95" and "Salcare® SC 96" by the company Allied Colloids.

(15) Other cationic polymers which can be used in the compositions of the present disclosure are polyalkyleneimines, such as, for example, polyethyleneimines, polymers containing vinylpyridine or vinylpyridinium units, condensates of polyamines and of epichlorohydrin, quaternary polyureylenes and chitin derivatives.

Among the cationic polymers which may be used in the context of the present disclosure, at least one embodiment uses the polymers of families (1), (9), (10), (11) and (14), and in at least one further embodiment, the polymers containing repeating units of formulae (W) and (U) below:

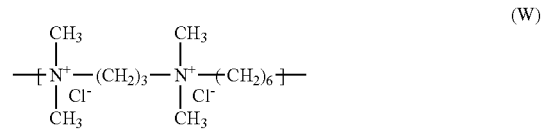

(W)

and, for example, those whose molecular weight, determined by gel permeation chromatography, ranges from 9,500 to 9,900;

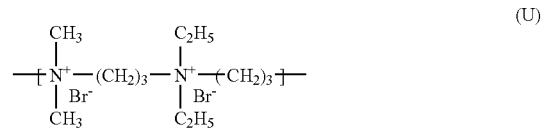

(U)

and, for example, those whose molecular weight, determined by gel permeation chromatography, is about 1,200.

Among the amphoteric polymers that may be used in accordance with at least one embodiment of the present disclosure, non-limiting mention may be made of those chosen from polymers comprising units K and M randomly distributed in the polymer chain, wherein K is chosen from units derived from a monomer comprising at least one basic nitrogen atom and M is chosen from units derived from an acidic monomer comprising at least one carboxylic or sulfonic groups, or alternatively K and M may be chosen from groups derived from zwitterionic carboxybetaine or sulfobetaine monomers;

K and M may also be chosen from cationic polymer chains comprising primary, secondary, tertiary or quaternary amine groups, wherein at least one of the amine groups bears a carboxylic or sulfonic group linked via a hydrocarbon-based radical, or alternatively K and M form part of a chain of a polymer containing an $\alpha,\beta$-dicarboxylic ethylene unit in which one of the carboxylic groups has been made to react with a polyamine comprising at least one group chosen from primary and secondary amine groups.

The amphoteric polymers corresponding to the above definition that may be used according to at least one embodiment are chosen from the following polymers:

(1) polymers resulting from the copolymerization of a monomer derived from a vinyl compound bearing a carboxylic group such as, for example, acrylic acid, methacrylic acid, maleic acid, $\alpha$-chloroacrylic acid, and from a substituted vinyl compound containing at least one basic atom, such as, for example, dialkylaminoalkyl methacrylate and acrylate, dialkylaminoalkylmethacrylamide and -acrylamide. Such compounds are described in U.S. Pat. No. 3,836,537. Non-limiting mention may also be made of the sodium acrylate/acrylamidopropyltrimethylammonium chloride copolymer sold under the name Polyquart KE 3033 by the company Henkel.

The vinyl compound may also be a dialkyldiallylammonium salt such as dimethyldiallylammonium chloride. The copolymers of acrylic acid and of the latter monomer are sold under the names Merquat 280, Merquat 295 and Merquat Plus 3330 by the company Calgon.

(2) Polymers containing units derived from:
a) at least one monomer chosen from acrylamides and methacrylamides substituted on the nitrogen with an alkyl radical,
b) at least one acidic comonomer containing at least one reactive carboxylic group, and
c) at least one basic comonomer such as esters containing primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides which may be used according to at least one embodiment of the disclosure include groups in which the alkyl radicals contain from 2 to 12 carbon atoms such as, for example, N-ethylacrylamide, N-tert-butylacrylamide, N-tert-octylacrylamide, N-octylacrylamide, N-decylacrylamide, N-dodecylacrylamide and the corresponding methacrylamides.

In at least one embodiment, the acidic comonomers are chosen from acrylic acid, methacrylic acid, crotonic acid, itaconic acid, maleic acid and fumaric acid and alkyl monoesters, having 1 to 4 carbon atoms, of maleic or fumaric acids or anhydrides.

In at least one embodiment of the present disclosure, the basic comonomers are chosen from aminoethyl, butylaminoethyl, N,N'-dimethylaminoethyl and N-tert-butylaminoethyl methacrylates.

The copolymers whose CTFA (4th edition, 1991) name is Octylacrylamide/acrylates/butylaminoethyl methacrylate copolymer such as the products sold under the name Amphomer or Lovocryl 47 by the company National Starch may be used in at least one embodiment.

(3) Polyamino amides that are crosslinked and alkylated partially or totally derived from polyamino amides of general formula:

(X)

wherein $R_{19}$ is chosen from divalent radicals derived from a saturated dicarboxylic acid, a mono- or dicarboxylic aliphatic acid containing an ethylenic double bond, an ester of a lower alkanol, having 1 to 6 carbon atoms, of these acids or a radical derived from the addition of any one of the acids to a bis (primary) or bis(secondary)amine, and Z is chosen from bis (primary), mono- and bis(secondary)polyalkylene-polyamine radicals and, for example, is chosen from:

a) in an amount of from 60 to 100 mol %, the radical

(XI)

where $x=2$ and $p=2$ or 3, or alternatively $x=3$ and $p=2$ this radical being derived from diethylenetriamine, from triethylenetetraamine or from dipropylenetriamine;

b) in an amount ranging from 0 to 40 mol %, the radical (XI) above in which $x=2$ and $p=1$ and which is derived from ethylenediamine, or the radical derived from piperazine:

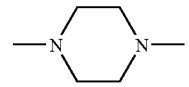

c) in an amount ranging from 0 to 20 mol %, the $-NH-(CH_2)_6-NH-$ radical derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

In at least one embodiment, the saturated carboxylic acids are chosen from acids having 6 to 10 carbon atoms, such as adipic acid, 2,2,4-trimethyladipic acid and 2,4,4-trimethyladipic acid, terephthalic acid and acids containing an ethylenic double bond, for instance acrylic acid, methacrylic acid and itaconic acid.

The alkane sultones used in the alkylation are chosen from, for example, propane sultone or butane sultone, and the salts of the alkylating agents are chosen from, for example, the sodium or potassium salts.

(4) Polymers containing zwitterionic units of formula:

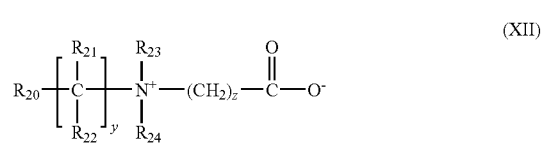
(XII)

wherein:
R$_{20}$ is chosen from polymerizable unsaturated groups such as acrylate, methacrylate, acrylamide and methacrylamide groups,
y and z are integers from 1 to 3,
R$_{21}$, and R$_{22}$ are chosen from hydrogen atoms, methyl radicals, ethyl radicals and propyl radicals, and
R$_{23}$ and R$_{24}$ are chosen from hydrogen atoms and alkyl radicals such that the sum of the carbon atoms in R$_{23}$ and R$_{24}$ does not exceed 10.

The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate.

By way of example, non-limiting mention may be made of the copolymer of butyl methacrylate/dimethyl carboxymethylammonio ethyl methacrylate such as the product sold under the name Diaformer Z301 by the company Sandoz.

(5) Chitosan-based polymers comprising monomer units chosen from those of formulae (XIII), (XIV) and (XV) below:

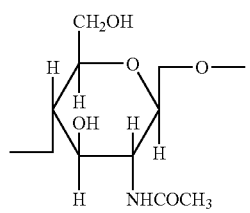

(XIII)

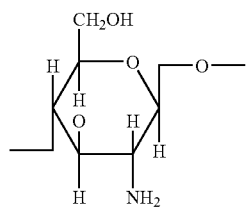

(XIV)

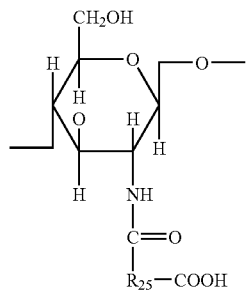

(XV)

the unit (XIII) being present in an amount ranging from 0 to 30%, the unit (XIV) in an amount ranging from 5% to 50% and the unit (XV) in an amount ranging from 30% to 90%, wherein, in the unit (XV), R$_{25}$ is a radical of formula:

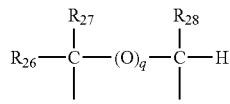

wherein:
if q=0, R$_{26}$, R$_{27}$ and R$_{28}$, which may be identical or different, each are chosen from hydrogen atoms, methyl, hydroxyl, acetoxy and amino residues, monoalkylamine residues, dialkylamine residues which are optionally interrupted by at least one nitrogen atom and/or optionally substituted with at least one group chosen from amine, hydroxyl, carboxyl, alkylthio and sulfonic groups, and alkylthio residues in which the alkyl group bears an amino residue, at least one of the radicals R$_{26}$, R$_{27}$ and R$_{28}$ being, in this case, a hydrogen atom;
or, if q=1, R$_{26}$, R$_{27}$ and R$_{28}$ each represent a hydrogen atom, and also the salts formed by these compounds with bases or acids.

(6) Polymers derived from the N-carboxyalkylation of chitosan, such as N-carboxymethylchitosan or N-carboxybutylchitosan sold under the name "Evalsan" by the company Jan Dekker.

(7) Polymers chosen from those of formula (XVI) such as those described, for example, in French Patent No. FR 1 400 366:

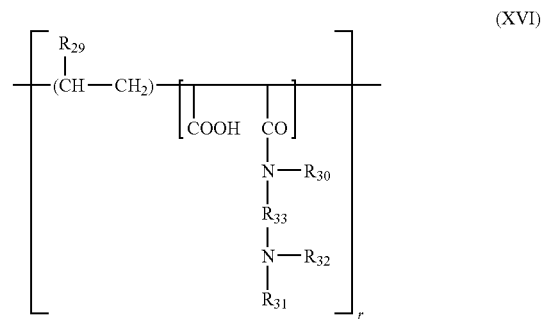

(XVI)

wherein
r is a number greater than 1,
R$_{29}$ is chosen from hydrogen atoms, CH$_3$O, CH$_3$CH$_2$O and phenyl radicals,
R$_{30}$ is chosen from hydrogen and lower alkyl radicals such as methyl or ethyl,
R$_{31}$ is chosen from hydrogen atoms and lower alkyl radicals such as methyl or ethyl,
R$_{32}$ is chosen from lower alkyl radicals such as methyl or ethyl or a radical corresponding to the formula: R$_{33}$—N(R$_{31}$)$_2$, R$_{33}$ chosen from —CH$_2$—CH$_2$—, —CH$_2$—CH$_2$—CH$_2$— and —CH$_2$—CH(CH$_3$)— groups, R$_{31}$ having the meanings mentioned above, and also the higher homologues of these radicals and containing up to 6 carbon atoms.

(8) Amphoteric polymers of the type -D-X-D-X- chosen from:
a) polymers obtained by the action of chloroacetic acid or sodium chloroacetate on compounds containing at least one unit of formula (XVII):

 (XVII)

where D is the radical

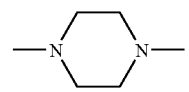

and X is the symbol E or E', wherein E or E', which may be identical or different, are chosen from divalent radicals which is an alkylene radical with a straight or branched chain containing up to 7 carbon atoms in the main chain, which is unsubstituted or substituted with hydroxyl groups and which can contain, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) polymers of formula (XVIII):

-D-X-D-X-                (XVIII)

where D is the radical

and X is chosen from the symbol E or E" and at least once E"; wherein E has the meaning given above and E" is chosen from divalent radicals which comprise an alkylene radical with a straight or branched chain having up to 7 carbon atoms in the main chain, which is unsubstituted or substituted with at least one hydroxyl radical and containing at least one nitrogen atom, the nitrogen atom being substituted with an alkyl chain which is optionally interrupted with an oxygen atom and necessarily containing at least one carboxyl functional group or at least one hydroxyl functional group and betainized by reaction with chloroacetic acid or sodium chloroacetate.

(9) ($C_1$-$C_5$)alkyl vinyl ether/maleic anhydride copolymers partially modified by semi-amidation with an N,N-dialkylaminoalkylamine such as N,N-dimethylaminopropylamine or by semi-esterification with an N,N-dialkanolamine. These copolymers can also contain other vinyl comonomers such as vinylcaprolactam.

The amphoteric polymers that may be used in at least one embodiment according to the disclosure are those of family (1).

According to at least one embodiment of the present disclosure, the at least one cationic or amphoteric substantive polymer, when present, may be present in an amount ranging from 0.01% to 10% by weight relative to the weight of the dye composition, such as, for example, from 0.05% to 5% by weight relative to the weight of the dye composition or from 0.1% to 3% by weight relative to the weight of the dye composition.

In at least one embodiment, the medium that is suitable for dyeing may consist of water or comprise a mixture of water and at least one organic solvent to dissolve the compounds that are not sufficiently water-soluble. Examples of organic solvents that may be mentioned include $C_1$-$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and mixtures thereof.

The solvents may be present in amounts ranging from 1% to 40% by weight relative to the weight of the dye composition, such as, for example, from 5% to 30% by weight relative to the weight of the dye composition.

The composition may also comprise at least one adjuvant that is common in the field, such as, for example, nonionic surfactants other than those listed previously; anionic, amphoteric or zwitterionic surfactants; organic or mineral thickeners; antioxidants; penetrants; sequestrants; fragrances; buffers; dispersants; conditioning agents other than the cationic or amphoteric substantive polymers described above, for instance cations, or volatile or non-volatile, modified or unmodified silicones; film-forming agents; ceramides; preserving agents; stabilizers; and opacifiers.

A person skilled in the art will take care to select any optional additional compound(s) such that the beneficial properties intrinsically associated with the composition in accordance with the disclosure are not, or are not substantially, adversely affected by the envisaged addition(s).

The present disclosure also relates to a process for dyeing keratin materials using the composition according to the present disclosure.

According to at least one embodiment, the process comprises applying the composition in the absence of an oxidizing agent, to keratin materials, which may be wet or dry fibers, with or without final rinsing of the composition.

In these embodiments, the composition according to the present disclosure does not comprise any oxidation dye precursor, but only at least one direct dyes.

According to at least one other embodiment, the process comprises applying the composition according to the present disclosure, in the presence of an oxidizing agent, to wet or dry keratin materials, and then leaving it on for a period that is sufficient to obtain the desired coloration, such as a predetermined period of time.

According to at least one embodiment, at least one dye composition according to the present disclosure and an oxidizing composition are applied to the keratin fibers simultaneously or successively without intermediate rinsing.

In at least one other embodiment, the composition applied is a "ready-to-use composition", i.e., a composition obtained by extemporaneous mixing of at least one dye composition according to the present disclosure with a composition comprising at least one oxidizing agent.

In this case, the dye composition may comprise at least one oxidation dye precursor. It may also comprise at least one direct dye, when lightening of the keratin fibers is desired in combination with dyeing.

According to the present disclosure, the dye composition may comprise a combination of oxidation dye precursors and of direct dyes.

The at least one oxidizing agent present in the oxidizing composition may be chosen, for example, from hydrogen peroxide, urea peroxide, alkali metal bromates, persalts such as perborates and persulfates, and enzymes such as peroxidases and two-electron or four-electron oxidoreductases. Hydrogen peroxide is used in at least one embodiment.

The at least one oxidizing agent may be present in an amount ranging from 1% to 40% by weight relative to the weight of the ready-to-use composition, such as, for example, from 1% to 20% by weight relative to the weight of the ready-to-use composition.

In at least one embodiment, the oxidizing composition used is an aqueous composition and may be in the form of a solution or an emulsion.

In at least one embodiment, the composition free of oxidizing agent may be mixed with about 0.5 to 10 weight equivalents of the oxidizing composition.

In at least one embodiment according to the present disclosure, the pH of the ready-to-use composition ranges from 3 to 12, such as, for example, from 4 to 11 or from 6.5 to 10.5.

The pH of the ready-to-use composition may be adjusted using a basifying or acidifying agent chosen, for example, from those mentioned previously.

In embodiments where the composition is applied in the presence of an oxidizing agent, the process may comprise a preliminary step that comprises separately storing, in at least one first compartment, at least one dye composition according to the present disclosure and, in at least one second compartment, a composition comprising at least one oxidizing agent in a medium that is suitable for dyeing human keratin fibers, and then mixing them together at the time of use, before applying this mixture to the wet or dry keratin materials.

Irrespective of the specific process steps used, i.e., in the presence or absence of oxidizing agent, the time required to develop the coloration may range from a few seconds to 60 minutes, such as, for example, from 1 to 50 minutes.

The temperature required to develop the coloration may range from room temperature (15 to 25° C.) to 250° C., such as, for example, from room temperature to 180° C. or from room temperature to 60° C.

Once the time required to develop the coloration has elapsed, the composition may be removed.

This may take place in a conventional manner, either by performing at least one rinsing operation, or by performing at least one washing and rinsing operation, or by performing a combination thereof. Finally, the keratin materials may be dried or left to dry.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the disclosure as approximations, the numerical values set forth in the specific examples are reported as precisely as possible. Any numerical value, however, inherently contains certain errors necessarily resulting from the standard deviation found in its respective testing measurement.

The examples that follow are given as illustrations of the present disclosure without, however, being limiting in nature.

EXAMPLES

The dye compositions of the disclosure below were prepared (amounts expressed in grams):

|  | A | B | C |
|---|---|---|---|
| Double-distilled pure cetyl alcohol (Lanette 16; from Cognis) | 10.2 | 10.2 | 10.2 |
| Polyglycerolated (2 mol) oleyl alcohol | 4 | 4 | — |
| Oxyethylenated (10 OE) oleyl alcohol (Brij 96 V; from Uniquema) | — | — | 4 |
| Glyceryl stearate (Tegin 6070; from Goldschmidt) | 5.8 | 5.8 | 5.8 |
| Decyl oleate (Cetiol V; from Cognis) | — | 1.8 | — |
| Glycol distearate (Tegin BL 315; from Goldschmidt) | 1.8 | — | 1.8 |
| Oleic acid | 2.73 | 2.73 | 2.73 |
| Pure monoethanolamine | 0.52 | 0.52 | 0.52 |

-continued

|  | A | B | C |
|---|---|---|---|
| Hydroxyethylcellulose quaternized with substituted lauryldimethylammonium epoxide (polyquaternium-24; Quatrisoft LM 200; from Amerchol) | — | — | 0.05 |
| Cationic polyurethane (Polyurethane 16 - INCI name) | 0.1 | 0.1 | — |
| Polydimethyldiallylammonium chloride at 40% in water, non-stabilized (polyquaternium-6) | — | — | 2 |
| Sodium metabisulfite | — | — | 0.71 |
| Ammonium thiolactate as an aqueous 58% solution | 0.8 | 0.8 | — |
| Ascorbic acid | 0.25 | 0.25 | 0.25 |
| Titanium oxide (untreated anatase) coated with polydimethylsiloxane (98/2) (CI: 77891) | 0.15 | 0.15 | 0.15 |
| Citric acid | 0.31 | 0.31 | 0.31 |
| Aqueous ammonia (20% ammonia) | 11.1 | 11.1 | 11.1 |
| 1-Hydroxy-4-aminobenzene | 0.545 | 0.545 | 0.545 |
| 1-Methyl-2-hydroxy-4-aminobenzene | 0.615 | 0.615 | 0.615 |
| Fragrance | 0.95 | 0.95 | 0.95 |
| Deionized water | 60.13 | 60.13 | 58.27 |

The above dye compositions were mixed at the time of use, in a plastic bowl and for 2 minutes, with an aqueous oxidizing composition containing 6% aqueous hydrogen peroxide solution, at a rate of 1 part of dye composition per 1.5 parts of oxidizing composition. The mixing was quick and easy.

Each mixture obtained was applied to locks of natural hair containing 90% white hairs, and was left on for 20 minutes.

The applications were quick and easy. The product stayed in place perfectly, did not run, and spread well from the root to the end.

The locks were then rinsed with water, washed with a standard shampoo, rinsed again with water, and then dried and disentangled.

The mixtures were satisfactorily removed upon rinsing.

The hair was dyed in a strong coppery red shade. Furthermore, the hair was not coarse.

What is claimed is:

1. A dye composition comprising, in a medium that is suitable for dyeing keratin fibers:
   at least one dye chosen from oxidation dye precursors and direct dyes;
   at least one nonionic surfactant chosen from oxyalkylenated nonionic surfactants and glycerolated nonionic surfactants;
   at least one cationic associative polymer;
   at least one fatty alcohol; and
   at least one fatty acid ester of a $C_1$-$C_{10}$ alcohol;
   wherein the fatty alcohol/nonionic surfactant weight ratio is greater than 0.5; and
   wherein the dye composition comprises water in an amount greater than or equal to 55% by weight relative to the weight of the dye composition.

2. The composition according to claim 1, wherein water is present in an amount greater than or equal to 60% by weight relative to the weight of the dye composition.

3. The composition according to claim 1, wherein the at least one nonionic surfactant is chosen from:
   oxyalkylenated fatty alcohols and glycerolated fatty alcohols;
   oxyalkylenated alkylphenols comprising a $C_8$-$C_{18}$ alkyl chain;
   oxyalkylenated fatty amides and glycerolated fatty amides;
   oxyalkylenated fatty amines;

oxyalkylenated plant oils;
optionally oxyalkylenated fatty acid esters of sorbitan;
optionally oxyalkylenated fatty acid esters of sucrose;
fatty acid esters of polyethylene glycol;
($C_6$-$C_{30}$)alkylpolyglycosides;
N—($C_6$-$C_{30}$)alkylglucamine derivatives;
amine oxides; and
copolymers of ethylene oxide and of propylene oxide.

4. The composition according to claim 3, wherein the amine oxides are chosen from ($C_{10}$-$C_{14}$)alkylamine oxides and N-acylaminopropylmorpholine oxides.

5. The composition according to claim 3, wherein the at least one nonionic surfactant is chosen from oxyalkylenated and glycerolated fatty alcohols.

6. The composition according to claim 1, wherein the at least one nonionic surfactant is present in an amount ranging from 0.01% to 50% by weight relative to the weight of the dye composition.

7. The composition according to claim 1, wherein the at least one fatty alcohol is present in an amount ranging from 0.1% to 30% by weight relative to the weight of the dye composition.

8. The composition according to claim 1, wherein the fatty alcohol/nonionic surfactant weight ratio is greater than 0.75.

9. The composition according to claim 1, wherein the at least one fatty acid ester of a $C_1$-$C_{10}$ alcohol is chosen from monoesters, diesters and triesters of linear and branched, saturated and unsaturated $C_8$-$C_{30}$ carboxylic acids and of linear and branched, saturated and unsaturated $C_1$-$C_{10}$ monohydroxylated and polyhydroxylated alcohols.

10. The composition according to claim 9, wherein the at least one fatty acid ester of a $C_1$-$C_{10}$ alcohol is chosen from the monoesters, diesters and triesters of oleic acid, lauric acid, palmitic acid, myristic acid, behenic acid, stearic acid, linoleic acid, linolenic acid, capric acid or arachidonic acid and of methanol, ethanol, propanol, isopropanol, ethylene glycol, glycerol, octanol and decanol.

11. The composition according to claim 1, wherein the at least one fatty acid ester of a $C_1$-$C_{10}$ alcohol is present in an amount ranging from 0.1% to 20% by weight relative to the weight of the dye composition.

12. The composition according to claim 1, wherein the at least one cationic associative polymer is chosen from quaternized cellulose derivatives, cationic polyurethanes, cationic polyvinyllactams and cationic acrylic terpolymers.

13. The composition according to claim 1, wherein the at least one cationic associative polymer is present in an amount ranging from 0.01% to 5% by weight relative to the weight of the dye composition.

14. The composition according to claim 1, wherein the at least one oxidation dye precursor is chosen from oxidation bases and couplers.

15. The composition according to claim 14, wherein the at least one oxidation base is present in an amount ranging from 0.0005% to 12% by weight relative to the weight of the dye composition.

16. The composition according to claim 14, wherein the at least one coupler is present in an amount ranging from 0.0001% to 15% by weight relative to the weight of the dye composition.

17. The composition according to claim 1, wherein the at least one direct dye is present in an amount ranging from 0.0005% to 15% by weight relative to the weight of the dye composition.

18. The composition according to claim 1, further comprising at least one basifying agent.

19. The composition according to claim 18, wherein the at least one basifying agent is chosen from aqueous ammonia, alkanolamines and combinations of $C_2$-$C_{10}$ alkanolamines with alkali metal or alkaline-earth metal silicates.

20. The composition according to claim 1, further comprising at least one substantive polymer chosen from cationic and amphoteric substantive polymers.

21. The composition according to claim 20, wherein the at least one cationic or amphoteric substantive polymer is present in an amount ranging from 0.01% to 10% by weight relative to the weight of the dye composition.

22. The composition according to claim 1, further comprising at least one oxidizing agent.

23. A process for dyeing keratin fibers, comprising applying a dye composition to the keratin fibers, which may be wet or dry, wherein the dye composition comprises, in a medium that is suitable for dyeing keratin fibers:
at least one dye chosen from oxidation dye precursors and direct dyes;
at least one nonionic surfactant chosen from oxyalkylenated nonionic surfactants and glycerolated nonionic surfactants;
at least one cationic associative polymer;
at least one fatty alcohol; and
at least one fatty acid ester of a $C_1$-$C_{10}$ alcohol;
wherein the fatty alcohol/nonionic surfactant weight ratio is greater than 0.5; and
wherein the dye composition comprises water in an amount greater than or equal to 55% by weight relative to the weight of the dye composition.

24. A process for dyeing keratin fibers, comprising:
applying a dye composition to the keratin fibers, which may be wet or dry, in the presence of an oxidizing composition comprising at least one oxidizing agent, wherein the oxidizing composition is applied simultaneously with or successively to the dye composition without intermediate rinsing, wherein the dye composition comprises, in a medium that is suitable for dyeing keratin fibers:
at least one dye chosen from oxidation dye precursors and direct dyes;
at least one nonionic surfactant chosen from oxyalkylenated nonionic surfactants and glycerolated nonionic surfactants;
at least one cationic associative polymer;
at least one fatty alcohol; and
at least one fatty acid ester of a $C_1$-$C_{10}$ alcohol;
wherein the fatty alcohol/nonionic surfactant weight ratio is greater than 0.5; and
wherein the dye composition comprises water in an amount greater than or equal to 55% by weight relative to the weight of the dye composition;
leaving the mixture on the fibers for a predetermined period of time; and
rinsing the fibers.

25. The process according to claim 24, wherein the dye composition and oxidizing composition are mixed before application to the keratin fibers.

26. A multi-compartment kit for dyeing keratin fibers, comprising
at least one first compartment containing a dye composition comprising, in a medium that is suitable for dyeing keratin fibers:
at least one dye chosen from oxidation dye precursors and direct dyes;

at least one nonionic surfactant chosen from oxyalkylenated nonionic surfactants and glycerolated nonionic surfactants;
at least one cationic associative polymer;
at least one fatty alcohol; and
at least one fatty acid ester of a $C_1$-$C_{10}$ alcohol;
wherein the fatty alcohol/nonionic surfactant weight ratio is greater than 0.5; and
wherein the dye composition comprises water in an amount greater than or equal to 55% by weight relative to the weight of the dye composition; and
at least one second compartment containing an oxidizing composition comprising at least one oxidizing agent.

* * * * *